(12) United States Patent
Ben-David et al.

(10) Patent No.: US 9,102,975 B2
(45) Date of Patent: Aug. 11, 2015

(54) MEANS AND METHODS FOR DETECTING BACTERIA IN A SAMPLE

(75) Inventors: Moshe Ben-David, Tel-Aviv (IL);
Gallya Gannot, Ramat Hasharon (IL);
Tomer Eruv, Kfar Tapuah (IL)

(73) Assignee: OPTICUL DIAGNOSTICS LTD., Jerusalem (IL)

( * ) Notice: Subject to any disclaimer, the term of this patent is extended or adjusted under 35 U.S.C. 154(b) by 903 days.

(21) Appl. No.: 12/594,780

(22) PCT Filed: Apr. 6, 2008

(86) PCT No.: PCT/IL2008/000472
§ 371 (c)(1),
(2), (4) Date: Oct. 20, 2009

(87) PCT Pub. No.: WO2008/122975
PCT Pub. Date: Oct. 16, 2008

(65) Prior Publication Data
US 2010/0099139 A1    Apr. 22, 2010

Related U.S. Application Data

(60) Provisional application No. 60/921,730, filed on Apr. 4, 2007.

(51) Int. Cl.
| | |
|---|---|
| G01N 33/48 | (2006.01) |
| G01N 31/00 | (2006.01) |
| G01N 33/50 | (2006.01) |
| C12Q 1/04 | (2006.01) |
| G06F 19/26 | (2011.01) |
| G06F 19/12 | (2011.01) |
| G06F 19/24 | (2011.01) |
| G01N 21/31 | (2006.01) |

(52) U.S. Cl.
CPC ........ *C12Q 1/04* (2013.01); *G01N 21/31* (2013.01); *G06F 19/12* (2013.01); *G06F 19/24* (2013.01); *G06F 19/26* (2013.01)

(58) Field of Classification Search
None
See application file for complete search history.

(56) References Cited

U.S. PATENT DOCUMENTS

| 4,847,198 A | 7/1989 | Nelson et al. |
| 5,734,587 A | 3/1998 | Backhaus et al. |

(Continued)

FOREIGN PATENT DOCUMENTS

| DE | 10051806 A1 | 10/2000 |
| EP | 0644412 A2 | 3/1995 |
| WO | 9841842 A1 | 9/1998 |

OTHER PUBLICATIONS

Short (IEEE Transactions on Information Theory, vol. IT-27, No. 5, Sep. 1981).*

(Continued)

*Primary Examiner* — Russell S Negin
(74) *Attorney, Agent, or Firm* — Paul D. Bianco; Martin Fleit; Fleit Gibbons Gutman Bongini & Bianco PL

(57) ABSTRACT

The present invention provides a method for detecting and/or identifying specific bacteria within an uncultured sample. The method comprises steps selected inter alia from (a) obtaining an absorption spectrum (AS) of said uncultured sample; (b) acquiring the n dimensional volume boundaries for said specific bacteria; (c) data processing said AS; and, (d) detecting and/or identifying said specific bacteria if said m1 statistical correlation and/or said m features are within said n dimensional volume.

7 Claims, 29 Drawing Sheets

(56) References Cited

U.S. PATENT DOCUMENTS 6,379,920 B1    4/2002    El-Sayed et al.
6,599,715 B1    7/2003    Vanderberg et al.

OTHER PUBLICATIONS

Dziuba et al. (International Dairy Journal, vol. 17, p. 183-189, Print: Mar. 2007; Online May 12, 2006).*

Anderson et al. Introduction to Statistics: Concepts and Applications. New York: West Publishing Company, 1991, p. 71.*

Naumann, Infrared Spectroscopy in Microbiology, Encyclopedia of Analytical Chemistry, p. 102-131, 2000.

International Search Report published Dec. 18, 2008 for PCT/IL2008/000472 filed Apr. 6, 2008.

Written Opinion of the International Searching Authority published Oct. 4, 2009 for PCT/IL2008/000472 filed Apr. 6, 2008.

* cited by examiner

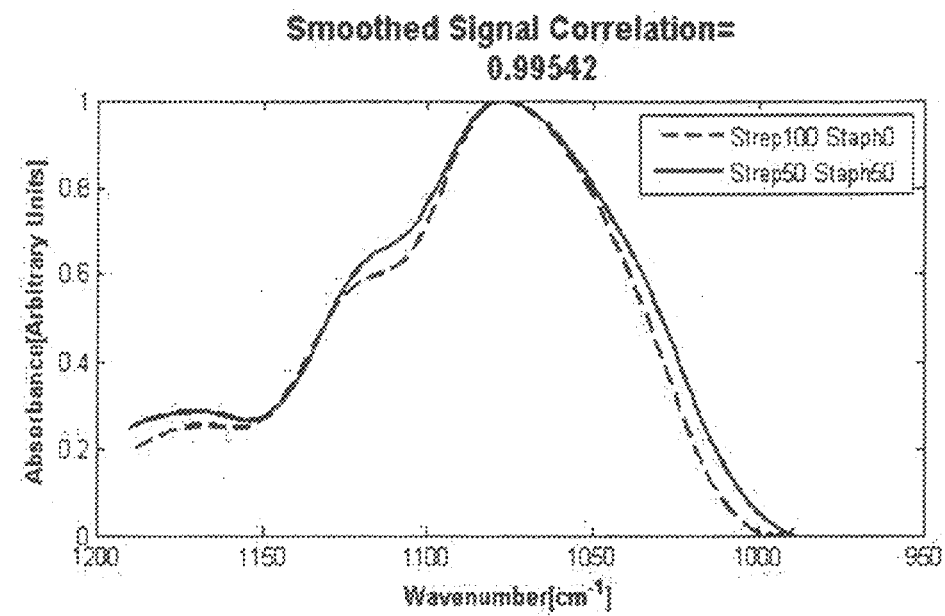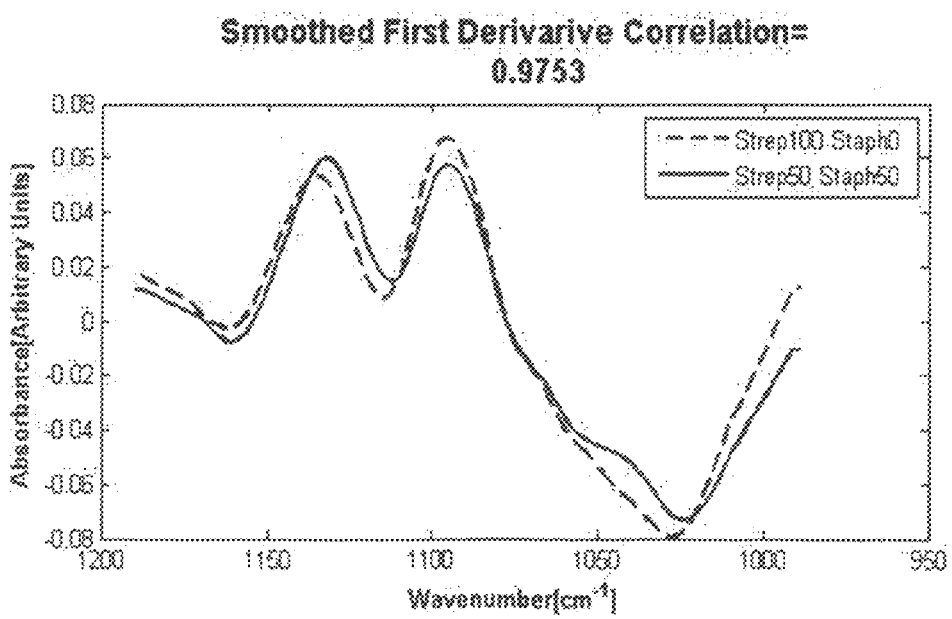
Fig 10.

MEANS AND METHODS FOR DETECTING BACTERIA IN A SAMPLE

FIELD OF THE INVENTION

The present invention relates to the field of spectroscopic medical diagnostics of specific bacteria within a sample. More particularly, the present invention provides a means and methods for detecting different kinds of bacteria in a sample by using spectroscopic measurements. The detection can be used for both medical and non-medical applications, such as detecting bacteria in water, beverages, food production, sensing for hazardous materials in crowded places etc.

BACKGROUND OF THE INVENTION

The identification of microorganisms is clearly of great importance in the medical fields. Furthermore, in recent years the need for efficient and relatively rapid identification techniques has become even more pressing owing to the remarkable expansion of environmental and industrial microbiology. One field in which it there is an urgent need for a rapid and accurate identification of bacteria is in the respiratory diseases.

Respiratory disease is an umbrella term for diseases of the lung, bronchial tubes, trachea and throat. These diseases range from mild and self-limited (coryza—or common cold) to being life-threatening, (bacterial pneumonia, or pulmonary embolism for example).

Respiratory diseases can be classified as either obstructive or restrictive. Obstructive is a condition which impede the rate of flow into and out of the lungs (e.g. asthma); and restrictive is a condition which cause a reduction in the functional volume of the lungs (e.g., pulmonary fibrosis).

Respiratory disease can be further classified as either upper or lower respiratory tract (most commonly used in the context of infectious respiratory disease), parenchymal and vascular lung diseases.

Infectious Respiratory Diseases are, as the name suggests, typically caused by one of many infectious agents able to infect the mammalian respiratory system, the etiology can be viral or bacterial (for example the bacterium *Streptococcus pneumoniae*).

A patient who suffers from infectious respiratory diseases will usually endure sore throat and have trouble swallowing. However, these symptoms might indicate also a flu.

Usually a throat culture is taken from the patient, that is suspected to have strep, in order to correctly diagnose the infection and to give the proper treatment.

The throat culture and bacterial analysis will usually take about three days. Moreover, the test causes some inconvenience to the patient.

The bacterial analysis will determine what is the desired and correct treatment and medication.

Another kind of tests are the "rapid" strep tests. In these tests a throat swab is inserted into a reagent and the presence of the bacteria is determined according to the chemical reaction between the bacteria and the reagent. Although these test give fast results (10 to 30 minutes) their sensitivity is very poor and they are not user friendly. Therefore they are not commonly used by the medical stuff.

Usually the physician desires to know if the bacteria is present and then prescribe antibiotics. Therefore, it will be beneficial for the doctor and the patient alike to get an immediate response for the throat sample.

An immediate response might be obtained by sampling the exhaled debrit (exhaled gases and micro fluids) of coughing or other human fluids (saliva, mucus etc.) and optically characterizing their content. Optically characterizing the sample will likely be more convenient for the patient than the usual throat culturing.

Some spectroscopic techniques already known in the art. For example, PCT No. WO 98/41842 to NELSON, Wilfred discloses a system for the detection of bacteria antibody complexes. The sample to be tested for the presence of bacteria is placed in a medium which contains antibodies attached to a surface for binding to specific bacteria to form an antigen-antibody complex. The medium is contacted with an incident beam of light energy. Some of the energy is emitted from the medium as a lower resonance enhanced Raman backscattered energy. The detection of the presence or absence of the microorganism is based on the characteristic spectral peak of said microorganism. In other words PCT No. WO 98/41842 uses UV resonance Raman spectroscopy.

U.S. Pat. No. 6,599,715 to Laura A. Vanderberg relates to a process for detecting the presence of viable bacterial spores in a sample and to a spore detection system. The process includes placing a sample in a germination medium for a period of time sufficient for commitment of any present viable bacterial spores to occur. Then the sample is mixed with a solution of a lanthanide capable of forming a fluorescent complex with dipicolinic acid. Lastly, the sample is measured for the presence of dipicolinic acid.

U.S. Pat. No. 4,847,198 to Wilfred H. Nelson; discloses a method for the identification of a bacterium. Firstly, taxonomic markers are excited in a bacterium with a beam of ultra violet energy. Then, the resonance enhance Raman back scattered energy is collected substantially in the absence of fluorescence. Next, the resonance enhanced Raman back scattered energy is converted into spectra which corresponds to the taxonomic markers in said bacterium. Finally, the spectra are displayed and thus the bacterium may be identified.

U.S. Pat. No. 6,379,920 to Mostafa A. El-Sayed discloses a method to analyze and diagnose specific bacteria in a biologic sample by using spectroscopic means. The method includes obtaining the spectra of a biologic sample of a non-infected patient for use as a reference, subtracting the reference from the spectra of an infected sample, and comparing the fingerprint regions of the resulting differential spectrum with reference spectra of bacteria. Using this diagnostic technique, U.S. Pat. No. 6,379,920 claims to identify specific bacteria without culturing.

Naumann et al had demonstrated bacteria detection and classification in dried samples using FTIR spectroscopy [Naumann D. et al., "Infrared spectroscopy in microbiology", Encyclopedia of Analytical Chemistry, R. A. Meyers (Ed.) pp. 102-131, John Wiley & Sons Ltd, Chichester, 2000.]. Marshall et al had identifies live microbes using FTIR Raman spectroscopy [Marshall et al "Vibrational spectroscopy of extant and fossil microbes: Relevance for the astrobiological exploration of Mars", Vibrational Spectroscopy 41 (2006) 182-189]. Others methods involve fluorescence spectroscopy of a combination of the above.

None of the prior art literature discloses means and method that can quickly (without culturing) and accurately detect bacteria from a sample, and none demonstrates identification within a wet sample. Furthermore, non of the prior art literature discloses means and method that can eliminate the water influence from the sample so as to better detect the bacteria. Moreover all of the above require a skilled operator and/or, the use of reagents or a complicated sample preparation for the detection of bacteria.

Thus, there is a long felt need for means and method for an accurate bacteria identification from an uncultured sample especially wet samples without the use of reagents and/or complicated sample preparation.

SUMMARY OF THE INVENTION

It is one object of the present invention to provide a method for detecting and/or identifying specific bacteria within an uncultured sample. The method comprises steps selected inter alia from:
a. obtaining an absorption spectrum (AS) of said uncultured sample;
b. acquiring the n dimensional volume boundaries for said specific bacteria by
  i. obtaining at least one absorption spectrum (AS2) of samples containing said specific bacteria;
  ii. extracting x features from said AS2 selected from a group consisting of peaks wavelength, peaks height and widths, different peaks' intensity ratios or any combination thereof; said x is an integer higher or equal to one;
  iii. calculating at least one derivative of said AS2;
  iv. dividing said AS2 into several segments according to said x features;
  v. calculating the y statistical correlation of each of said segment; said y is an integer higher or equal to one;
  vi. defining n dimensional space; n equals the sum of said x features and said y statistical correlations;
  vii. assigning each one of said x feature and each one of said y correlation to said specific bacteria;
  viii. calculating the Gaussian distribution for each of said x feature and/or for each of said y statistical correlations; said Gaussian distributions defined the n dimensional volume in said n dimensional space;
  ix. determining said boundaries of said n dimensional volume by using technique selected from a group consisting of quadratic Gaussian classifier, k nearest neighbor, Bayesian classification or any combination thereof;
c. data processing said AS;
  i. noise reducing by using different smoothing techniques selected from a group consisting of running average savitzky-golay or any combination thereof;
  ii. extracting m features from said AS selected from a group consisting of peak's width, intensity, the ratio width/intensity, peak's wavelength, different peaks' intensity ratios, or any combination thereof; said m is an integer higher or equal to one;
  iii. dividing said AS into several segments according to said m features;
  iv. calculating the $m_1$ statistical correlation of each of said segment; said $m_1$ is an integer higher or equal to one; and,
d. detecting and/or identifying said specific bacteria if said $m_1$ statistical correlation and/or said m features are within said n dimensional volume.

It is another object of the present invention to provide the method as defined above, wherein said step (c) of data processing said AS additionally comprising steps of:
  i. calculating at least one of the $o^{th}$ derivative of said AS; said o is an integer greater than or equals 1;
  ii. extracting $m_2$ features from said $o^{th}$ derivative selected from a group consisting of peak's width, intensity, the ratio width/intensity, different peaks' intensity ratios, peak's wavelength or any combination thereof;
  iii. dividing said $o^{th}$ derivative into several segments according to said $m_2$ features;
  iv. calculating the $m_3$ statistical correlation in each of said segments; and,
  v. detecting and/or identifying said specific bacteria if said $m_1$ and/or $m_3$ statistical correlation and/or said m and/or said $m_2$ features are within said n dimensional volume.

It is another object of the present invention to provide the method as defined above, wherein said step of calculating the statistical correlation of each of said segment is performed by using Pearson's correlation coefficient.

It is another object of the present invention to provide the method as defined above, additionally comprising the step of selecting said specific bacteria selected from a group consisting of *Streptococcus Pyogenes*, Group C and G beta-hemolytic streptococci, *Corynebacterium haemolyticum*, Diphtheria and Ulcerans, *Neisseria Gonorrhoeae*, *Mycoplasma Pneumoniae*, *Yersinia Enterocolitica*, *Mycobacterium tuberculosis*, *Chlamydia Trachomatiss* and *Pneumoniae*, *Bordetella Pertussis*, *Legionella* spp, *Pneumocystis Carinii*, *Nocardia*, *Histoplasma Capsulatum*, *Coccidioides Immitis*, *Haemophilus influenza* group A beta hemolytic and *staphylococcus Aureus*.

It is another object of the present invention to provide the method as defined above, wherein said step of obtaining the AS additionally comprising steps of:
a. providing at least one optical cell accommodates said uncultured sample;
b. providing p light source selected from a group consisting of laser, lamp, LEDs tunable lasers, monochrimator, p is an integer equal or greater than 1; said p light source are adapted to emit light to said optical cell;
c. providing detecting means for receiving the spectroscopic data of said sample;
d. emitting light from said light source at different wavelength to said optical cell; and,
e. collecting said light exiting from said optical cell by said detecting means; thereby obtaining said AS.

It is another object of the present invention to provide the method as defined above, wherein said step of emitting light is performed at the wavelength range of UV, visible, IR, mid-IR, far-IR and terahertz.

It is another object of the present invention to provide the method as defined above, additionally comprising the step of detecting said bacteria by analyzing said AS in the region of about 3000-3300 $cm^{-1}$ and/or about 850-1000 $cm^{-1}$ and/or about 1300-1350 $cm^-$.

It is another object of the present invention to provide a method for detecting and/or identifying specific bacteria within an uncultured sample. The method comprises steps selected inter alia from:
a. obtaining an absorption spectrum (AS) of said uncultured sample; said AS containing water influence;
b. acquiring the n dimensional volume boundaries for said specific bacteria by
  i. obtaining at least one absorption spectrum (AS2) of samples containing said specific bacteria;
  ii. extracting x features from said AS2 selected from a group consisting of peaks wavelength, peaks height and widths, different peaks' intensity ratios or any combination thereof; said x is an integer higher or equal to one;
  iii. calculating at least one derivative of said AS2;
  iv. dividing said AS2 into several segments according to said x features;
  v. calculating the y statistical correlation of each of said segment; said y is an integer higher or equal to one;
  vi. defining n dimensional space; n equals the sum of said x features and said y statistical correlations;

vii. assigning each one of said x feature and each one of said y correlation to said specific bacteria;
viii. calculating the Gaussian distribution for each of said x feature and/or for each of said y statistical correlations; said Gaussian distributions defined the n dimensional volume in said n dimensional space;
ix. determining said boundaries of said n dimensional volume by using technique selected from a group consisting of quadratic Gaussian classifier, k nearest neighbor, Bayesian classification or any combination thereof;

c. eliminating said water influence from said AS;
i. providing the absorption intensity at each of wavenumber $\tilde{v}$ within said AS ($Sig_{with\ water}(\tilde{v})$);
ii. dividing said AS into at least two wavenumber ranges;
iii. calculating the correction factors (CF) at each wavenumber $\tilde{v}$ within said least two ranges ($CF(\tilde{v})$);
iv. acquiring from said AS at least one absorption intensity that is mainly influenced by said water $Sig_{water\ only}(\tilde{v}_q)$ and the corresponding wavenumbers ($\tilde{v}_q$);
v. calculating at least one correction factor of said water ($CF_{water\ only}(\tilde{v}_q)$) at said at least one wavenumber ($\tilde{v}_q$);
vi. dividing said at least one $Sig_{water\ only}(\tilde{v}_q)$ by said at least one $CF_{water}(Sig_{water\ only}(\tilde{v}_q)/CF_{water\ only}(\tilde{v}_q)$ at said at least one wavenumber $\tilde{v}_q$;
vii. calculating the average of step (vi) ($AVG[Sig_{water\ only}(\tilde{v}_q)/CF_{water\ only}(\tilde{v}_q)]$);
viii. multiplying said $AVG[Sig_{water\ only}(\tilde{v}_q)/CF_{water\ only}(\tilde{v}_q)]$ by said $CF(\tilde{v})$ for each of said wavenumber $\tilde{v}$ within said AS; and,
ix. subtracting the result of step (viii) from said ($Sig_{with\ water}(\tilde{v})$) at each of said wavenumber $\tilde{v}$ within said AS;

d. data processing said AS without said water influence by
i. noise reducing by using different smoothing techniques selected from a group consisting of running average savitzky-golay or any combination thereof;
ii. extracting m features from said AS selected from a group consisting of peak's width, intensity, the ratio width/intensity, peak's wavelength, different peaks' intensity ratios, or any combination thereof; said m is an integer higher or equal to one;
iii. dividing said AS into several segments according to said m features;
iv. calculating the $m_1$ statistical correlation of each of said segment; said $m_1$ is an integer higher or equal to one; and, e. detecting and/or identifying said specific bacteria if said $m_1$ statistical correlation and/or said m features are within said n dimensional volume.

It is another object of the present invention to provide the method as defined above, wherein said step (c) of data processing said AS without said water influence, additionally comprising steps of:
i. calculating at least one of the $o^{th}$ derivative of said AS; said o is an integer greater than or equals 1;
ii. extracting $m_2$ features from said $o^{th}$ derivative selected from a group consisting peak's width, intensity, the ratio width/intensity, different peaks' intensity ratios, peak's wavelength or any combination thereof;
iii. dividing said $o^{th}$ derivative into several segments according to $m_2$ features;
iv. calculating the $m_3$ statistical correlation in each of said segments; and,
v. detecting and/or identifying said specific bacteria if said $m_1$ and/or $m_3$ statistical correlation and/or said m and/or said $m_2$ features are within said n dimensional volume.

It is another object of the present invention to provide the method as defined above, wherein said step of calculating the statistical correlation in each of said segments is performed by using Pearson's correlation coefficient.

It is another object of the present invention to provide the method as defined above, additionally comprising the step of selecting said specific bacteria selected from a group consisting of *Streptococcus Pyogenes*, Group C and G beta-hemolytic streptococci, *Corynebacterium haemolyticum*, Diphtheria and Ulcerans, *Neisseria Gonorrhoeae*, *Mycoplasma Pneumoniae*, *Yersinia Enterocolitica*, *Mycobacterium tuberculosis*, *Chlamydia Trachomatiss* and *Pneumoniae*, *Bordetella Pertussis*, *Legionella* spp, *Pneumocystis Carinii*, *Nocardia*, *Histoplasma Capsulatum*, *Coccidioides Immitis*, *Haemophilus influenza* group A beta hemolytic and *staphylococcus Aureus*.

It is another object of the present invention to provide the method as defined above, wherein said step of obtaining the AS additionally comprising steps of:
a. providing at least one optical cell accommodating said uncultured sample;
b. providing p light source selected from a group consisting of laser, lamp, LEDs tunable lasers, monochrimator, p is an integer equal or greater than 1; said p light source are adapted to emit light to said optical cell;
c. providing detecting means for receiving the spectroscopic data of said sample;
d. emitting light from said light source at different wavelength to said optical cell;
e. collecting said light exiting from said optical cell by said detecting means; thereby obtaining said AS.

It is another object of the present invention to provide the method as defined above, wherein said step of emitting light is performed at the wavelength range of UV, visible, IR, mid-IR, far IR and terahertz.

It is another object of the present invention to provide a system 1000 adapted to detect and/or identify specific bacteria within a sample. The system comprises:
a. means 100 for obtaining an absorption spectrum (AS) of said sample;
b. statistical processing means 200 for acquiring the n dimensional volume boundaries for said specific bacteria; said means 200 are characterized by
i. means 201 for obtaining at least one absorption spectrum (AS2) of samples containing said specific bacteria;
ii. means 202 for extracting x features from said AS2 selected from a group consisting of peaks wavelength, peaks height and widths, different peaks' intensity ratios or any combination thereof; said x is an integer higher or equal to one;
iii. means 203 for calculating at least one derivative of said AS2;
iv. means 204 for dividing said AS2 into several segments according to said x features;
v. means 205 for calculating the y statistical correlation of each of said segment; said y is an integer higher or equal to one;
vi. means 206 for defining n dimensional space; n equals the sum of said x features and said y statistical correlations;
vii. means 207 for assigning each one of said x feature and each one of said y correlation to said specific bacteria;

viii. means 208 for calculating the Gaussian distribution for each of said x feature and/or for each of said y statistical correlations; said Gaussian distributions defined the n dimensional volume in said n dimensional space;

ix. means 209 for determining said boundaries of said n dimensional volume by using technique selected from a group consisting of quadratic Gaussian classifier, k nearest neighbor, Bayesian classification or any combination thereof;

c. means 300 for data processing said AS; said means 300 are characterized by i. means 301 for noise reducing by using different smoothing techniques selected from a group consisting of running average savitzky-golay or any combination thereof;

ii. means 302 for extracting m features from said AS selected from a group consisting of peak's width, intensity, the ratio width/intensity, peak's wavelength, different peaks' intensity ratios, or any combination thereof; said m is an integer higher or equal to one;

iii. means 303 for dividing said AS into several segments according to said m features;

iv. means 304 for calculating the $m_1$ statistical correlation of each of said segment; said $m_1$ is an integer higher or equal to one; and, d. means 400 for detecting and/or identifying said specific bacteria if said $m_1$ statistical correlation and/or said m features are within said n dimensional volume.

It is another object of the present invention to provide the system as defined above, wherein said means 300 for data processing said AS additionally characterized by:

i. means 305 for calculating at least one of the $o^{th}$ derivative of said AS; said o is an integer greater than or equals 1;

ii. means 306 for extracting $m_2$ features from said $o^{th}$ derivative selected from a group consisting of peak's width, intensity, the ratio width/intensity, different peaks' intensity ratios, peak's wavelength or any combination thereof;

iii. means 307 for dividing said $o^{th}$ derivative into several segments according to said $m_2$ features;

iv. means 308 for calculating the $m_3$ statistical correlation in each of said segments; and, v. means 309 for detecting and/or identifying said specific bacteria if said $m_1$ and/or $m_3$ statistical correlation and/or said m and/or said $m_2$ features are within said n dimensional volume.

It is another object of the present invention to provide the system as defined above, wherein said means 308 or 304 for calculating the statistical correlation is selected from a group consisting of Pearson's correlation coefficient.

It is another object of the present invention to provide the system as defined above, wherein said specific bacteria is selected from a group consisting of *Streptococcus Pyogenes*, Group C and G beta-hemolytic streptococci, *Corynebacterium haemolyticum*, Diphtheria and Ulcerans, *Neisseria Gonorrhoeae, Mycoplasma Pneumoniae, Yersinia Enterocolitica, Mycobacterium tuberculosis, Chlamydia Trachomatiss* and *Pneumoniae, Bordetella Pertussis, Legionella* spp, *Pneumocystis Carinii, Nocardia, Histoplasma Capsulatum, Coccidioides Immitis, Haemophilus influenza* group A beta hemolytic and *staphylococcus Aureus*.

It is another object of the present invention to provide the system as defined above, wherein said means 100 for obtaining an absorption spectrum (AS) of said sample additionally comprising:

a. at least one optical cell for accommodating said uncultured sample;

b. p light source selected from a group consisting of laser, lamp, LEDs tunable lasers, monochrimator, p is an integer equal or greater than 1; said p light source are adapted to emit light at different wavelength to said optical cell; and, c. detecting means for receiving the spectroscopic data of said sample exiting from said optical cell.

It is another object of the present invention to provide the system as defined above, wherein said p light source are adapted to emit light at wavelength range selected from a group consisting of UV, visible, IR, mid-IR, far-IR and terahertz.

It is another object of the present invention to provide a system 2000 adapted to detect and/or identify specific bacteria within an uncultured sample; wherein said system 2000 comprising:

a. means 100 for obtaining an absorption spectrum (AS) of said uncultured sample; said AS containing water influence;

b. statistical processing means 200 for acquiring the n dimensional volume boundaries for said specific bacteria; said means 200 are characterized by i. means 201 for obtaining at least one absorption spectrum (AS2) of samples containing said specific bacteria;

ii. means 202 for extracting x features from said AS2 selected from a group consisting of peaks wavelength, peaks height and widths, different peaks' intensity ratios or any combination thereof; said x is an integer higher or equal to one;

iii. means 203 for calculating at least one derivative of said AS2;

iv. means 204 for dividing said AS2 into several segments according to said x features;

v. means 205 for calculating the y statistical correlation of each of said segment; said y is an integer higher or equal to one;

vi. means 206 for defining n dimensional space; n equals the sum of said x features and said y statistical correlations;

vii. means 207 for assigning each one of said x feature and each one of said y correlation to said specific bacteria;

viii. means 208 for calculating the Gaussian distribution for each of said x feature and/or for each of said y statistical correlations; said Gaussian distributions defined the n dimensional volume in said n dimensional space;

ix. means 209 for determining said boundaries of said n dimensional volume by using technique selected from a group consisting of quadratic Gaussian classifier, k nearest neighbor, Bayesian classification or any combination thereof;

c. means 300 for eliminating said water influence from said AS; said means 300 having:

i. means 301 for providing the absorption intensity at each of wavenumber $\tilde{v}$ within said AS ($Sig_{with\ water}(\tilde{v})$);

ii. means 302 for dividing said AS into at least two wavenumber ranges;

iii. means 303 for calculating the correction factors (CF) at each wavenumber $\tilde{v}$ within said least two ranges ($CF(\tilde{v})$);

iv. means 304 for acquiring from said AS at least one absorption intensity that is mainly influenced by water $Sig_{water\ only}(\tilde{v}_q)$ and the corresponding wavenumbers $(\tilde{v}_q)$;

v. means 305 for calculating at least one correction factor of said water $(CF_{water\ only}(\tilde{v}_q))$ at said at least one wavenumber $(\tilde{v}_q)$;

vi. means 306 for dividing said at least one $Sig_{water\ only}(\tilde{v}_q)$ by said at least one $CF_{water}$ $(Sig_{water\ only}(\tilde{v}_q)/CF_{water\ only}(\tilde{v}_q))$ at said at least one wavenumber $\tilde{v}_q$;

vii. means 307 for calculating the average of step (vi) $(AVG[Sig_{water\ only}(\tilde{v}_q)/CF_{water\ only}(\tilde{v}_q)])$;

viii. means 308 for multiplying said $AVG[Sig_{water\ only}(\tilde{v}_q)/CF_{water\ only}(\tilde{v}_q)]$ by said $CF(\tilde{v})$ for each of said wavenumber $\tilde{v}$ within said AS; and, ix. means 309 for subtracting the result of step (viii) from said $(Sig_{with\ water}(\tilde{v}))$ at each of said wavenumber $\tilde{v}$ within said AS;

d. means 400 for data processing said AS without said water influence; said means 400 are characterized by i. means 401 for noise reducing by using different smoothing techniques selected from a group consisting of running average savitzky-golay or any combination thereof;

ii. means 402 for extracting m features from said AS selected from a group consisting of peak's width, intensity, the ratio width/intensity, peak's wavelength, different peaks' intensity ratios, or any combination thereof; said m is an integer higher or equal to one;

iii. means 403 for dividing said AS into several segments according to said m features;

iv. means 404 for calculating the $m_1$ statistical correlation of each of said segment; said $m_1$ is an integer higher or equal to one; and, e. means 500 for detecting and/or identifying said specific bacteria if said $m_1$ statistical correlation and/or said m features are within said n dimensional volume.

It is another object of the present invention to provide the system as defined above, wherein said means 400 for data processing said AS without said water influence additionally comprising:

i. means 405 for calculating at least one of the $o^{th}$ derivative of said AS; said o is an integer greater than or equals 1;

ii. means 406 for extracting $m_2$ features from said $o^{th}$ derivative selected from a group consisting peak's width, intensity, the ratio width/intensity, different peaks' intensity ratios, peak's wavelength or any combination thereof;

iii. means 407 for dividing said $o^{th}$ derivative into several segments according to said $m_2$ features;

iv. means 408 for calculating the $m_3$ statistical correlation in each of said segments; and, v. means 409 for detecting and/or identifying said specific bacteria if said $m_1$ and/or $m_3$ statistical correlation and/or said m and/or said $m_2$ features are within said n dimensional volume.

It is another object of the present invention to provide the system as defined above, wherein said means 408 and/or 404 for calculating the statistical correlation in each of said segments is selected form a group consisting of Pearson's correlation coefficient. It is another object of the present invention to provide the system as defined above, wherein said specific bacteria is selected from a group consisting of *Streptococcus Pyogenes*, Group C and G beta-hemolytic streptococci, *Corynebacterium haemolyticum*, Diphtheria and Ulcerans, *Neisseria Gonorrhoeae, Mycoplasma Pneumoniae, Yersinia Enterocolitica, Mycobacterium tuberculosis, Chlamydia Trachomatiss* and *Pneumoniae, Bordetella Pertussis, Legionella* spp, *Pneumocystis Carinii, Nocardia, Histoplasma Capsulatum, Coccidioides Immitis, Haemophilus influenza* group A beta hemolytic and *staphylococcus Aureus*.

It is still an object of the present invention to provide the system as defined above, wherein said means 100 for obtaining an absorption spectrum (AS) of said sample additionally comprising:

a. at least one optical cell for accommodating said uncultured sample;

b. p light source selected from a group consisting of laser, lamp, LEDs tunable lasers, monochrimator, p is an integer equal or greater than 1; said p light source are adapted to emit light at different wavelength to said optical cell; and, c. detecting means for receiving the spectroscopic data of said sample exiting from said optical cell.

It is lastly an object of the present invention to provide the system as defined above, wherein said p light source are adapted to emit light at wavelength range selected from a group consisting of UV, visible, IR, mid-IR, far-IR and terahertz.

BRIEF DESCRIPTION OF THE FIGURES

In order to understand the invention and to see how it may be implemented in practice, a plurality of embodiments will now be described, by way of non-limiting example only, with reference to the accompanying drawings, in which

FIGS. 8-12 illustrate the absorption spectrum of a sample and a reference sample at wavenumber range of 950 cm$^{-1}$ to 1200 cm$^{-1}$ and the corresponding statistical correlation. FIGS. 8-12 also present the first derivative of the spectrum at the same range and the corresponding statistical correlation.

FIGS. 13-17 illustrate the absorption spectrum of a sample and a reference sample at wavenumber range of 1220 cm$^{-1}$ to 1380 cm$^{-1}$ and the corresponding statistical correlation. FIGS. 13-17 also present the first derivative of the spectrum at the same range and the corresponding statistical correlation.

Figure 24:
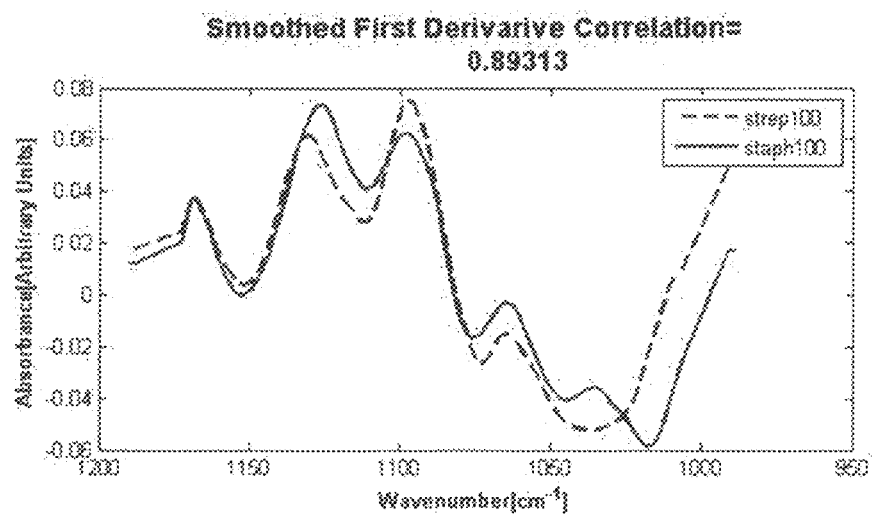
Figure 25:
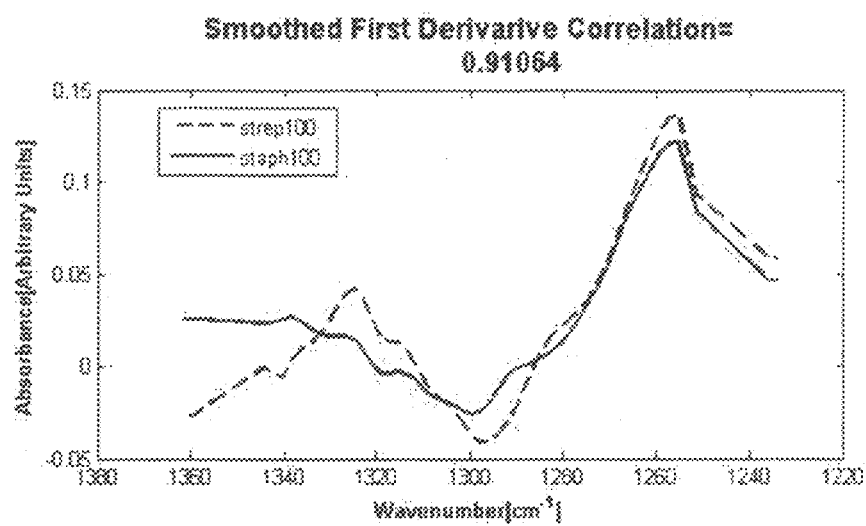
Figure 26:
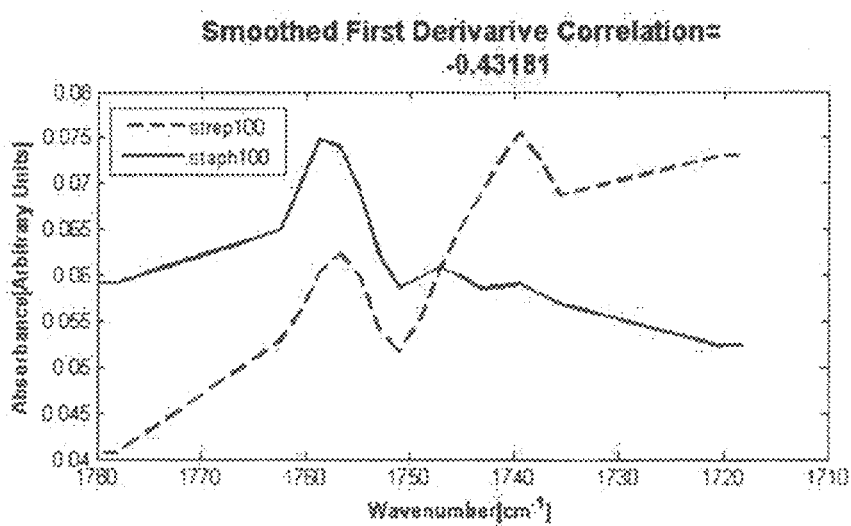

FIGS. 24-26 illustrate the first derivative of the absorption spectrum of a reference sample containing 100% *Streptococcus* and a solution containing 100% *Staphylococcus* and the correlation coefficient between them.

Figure 27:
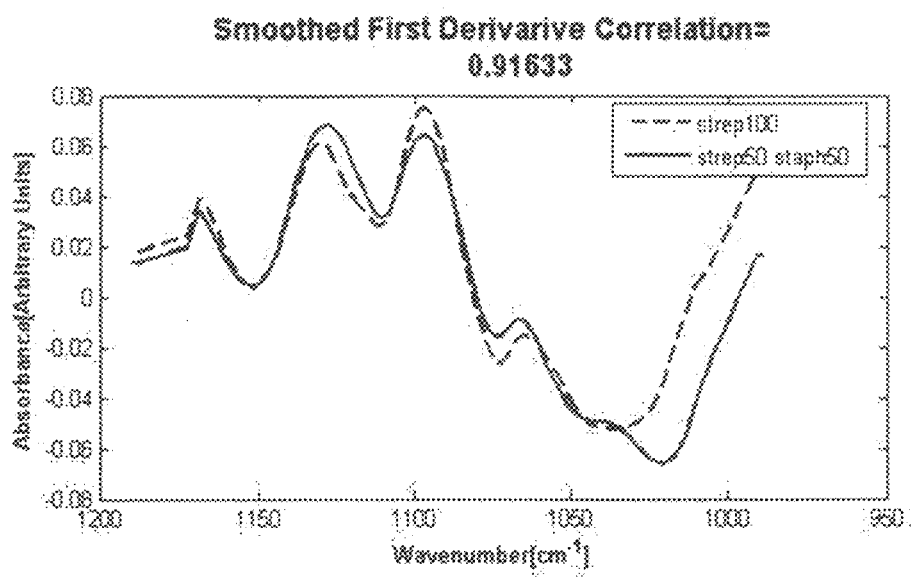
Figure 28:
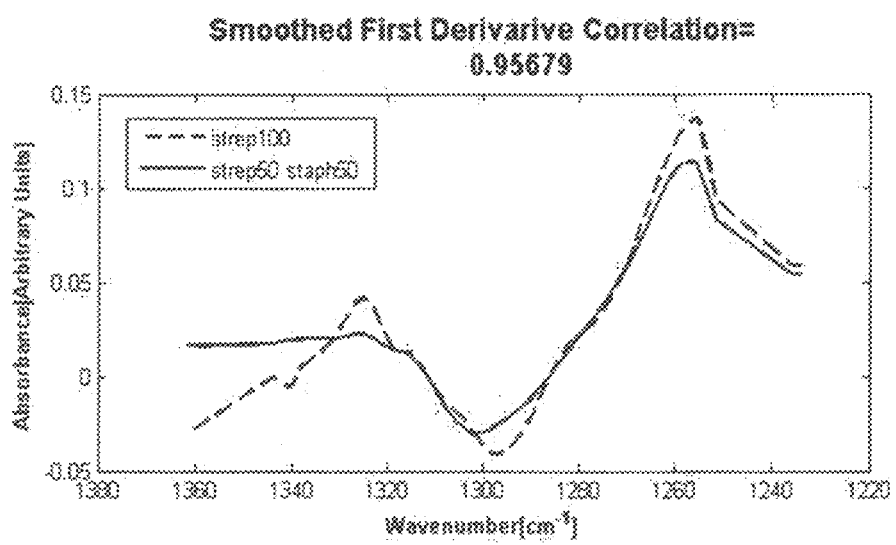
Figure 29:
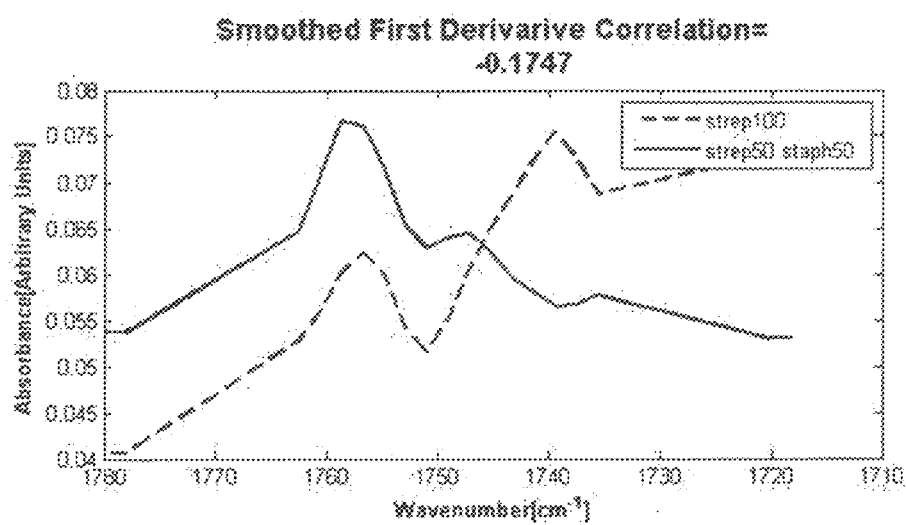

FIGS. 27-29 illustrate the first derivative of the absorption spectrum of a reference sample 100% *Streptococcus* and a solution containing 50% *Staphylococcus* and 50% *Streptococcus* and the correlation coefficient between them.

Figure 30:
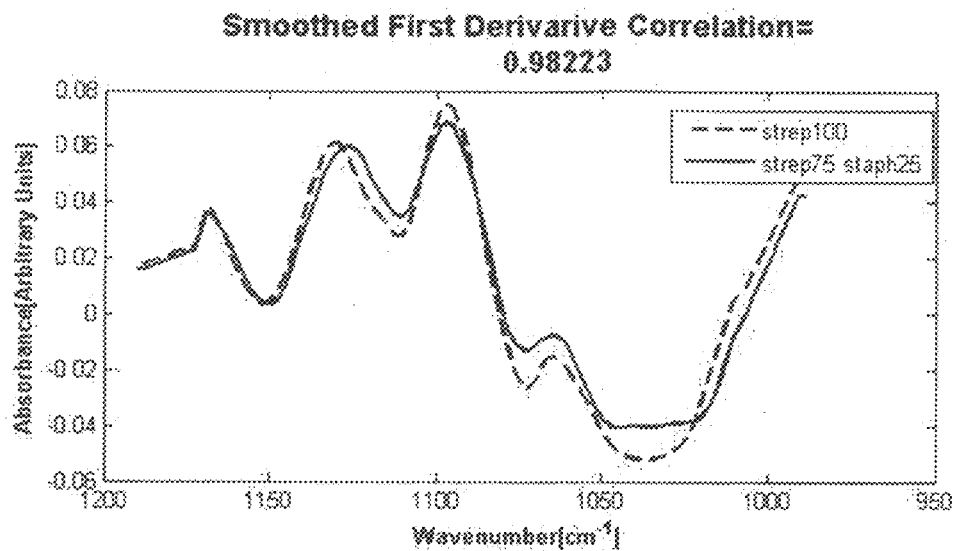
Figure 31:
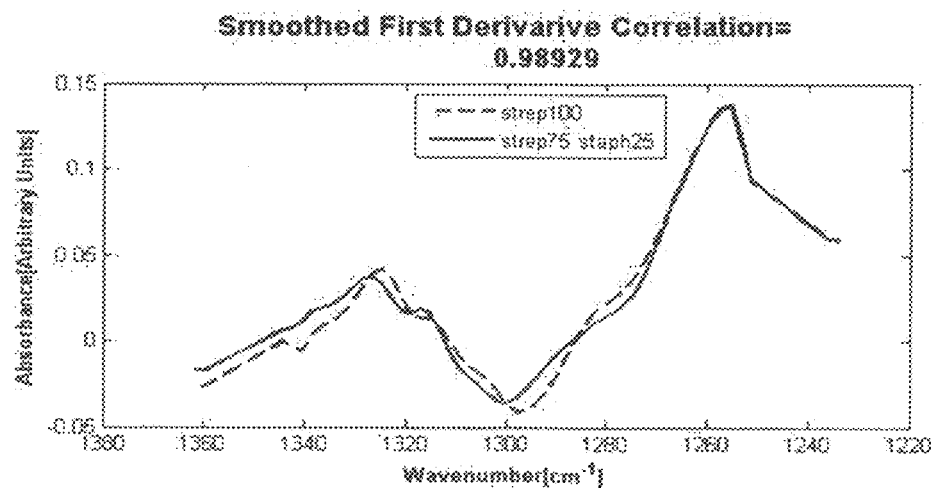
Figure 32:
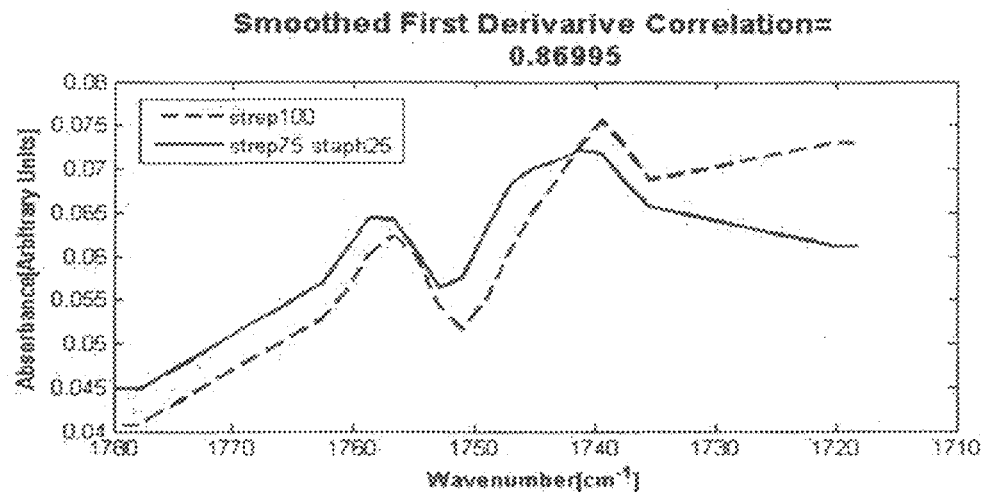

FIGS. 30-32 illustrate the first derivative of the absorption spectrum of a reference sample 100% *Streptococcus* and a solution containing 25% *Staphylococcus* and 75% *Streptococcus* and the correlation coefficient between them.

Figure 33:
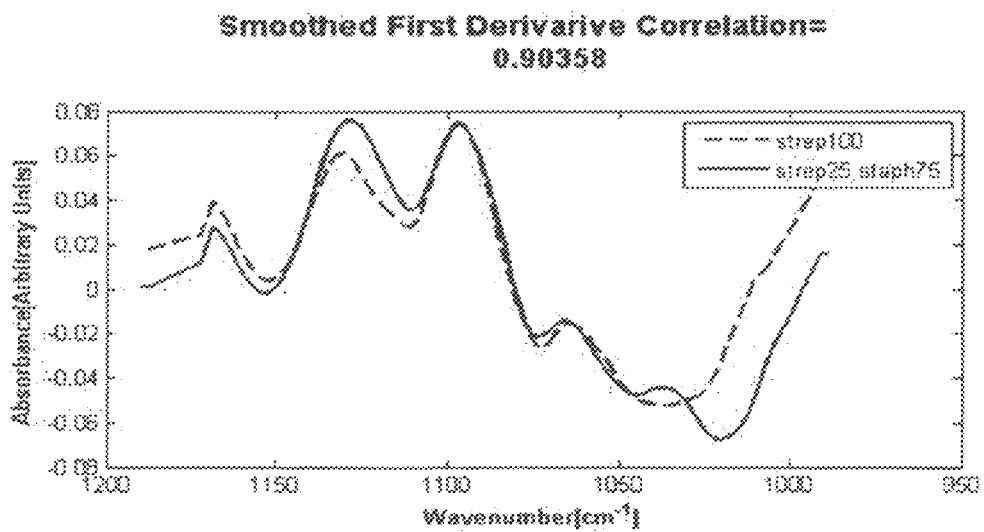
Figure 54:
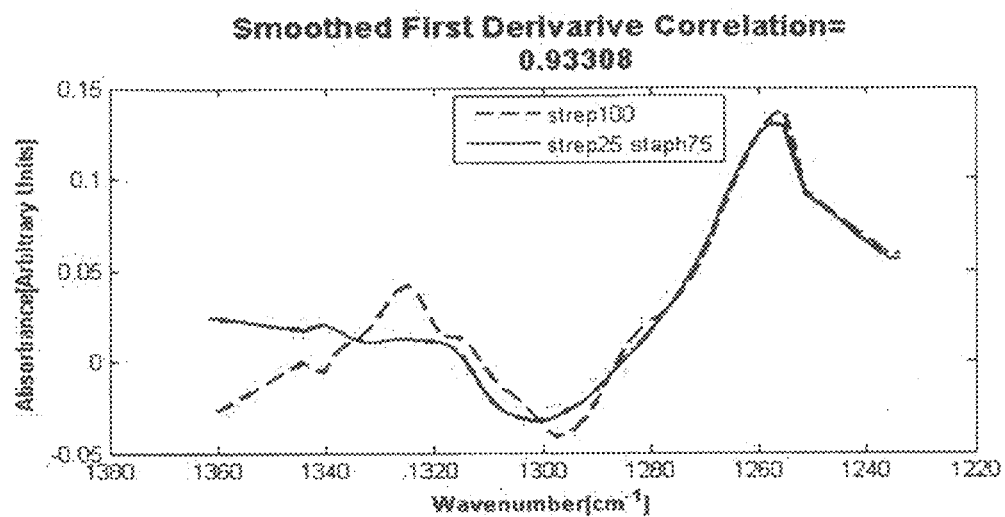
Figure 55:
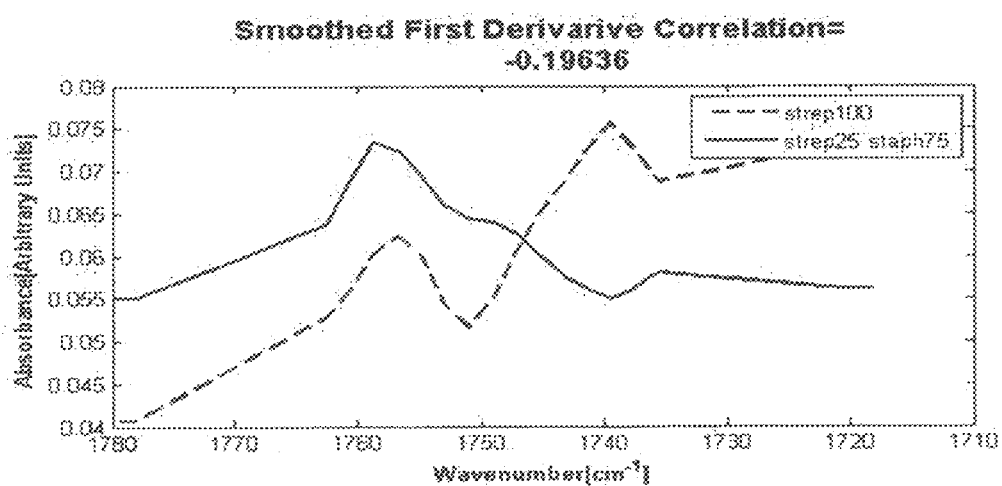

FIGS. 33-35 illustrate the first derivative of the absorption spectrum of a reference sample 100% *Streptococcus* and a solution containing 75% *Staphylococcus* and 25% *Streptococcus* and the correlation coefficient between them.

Figure 36:
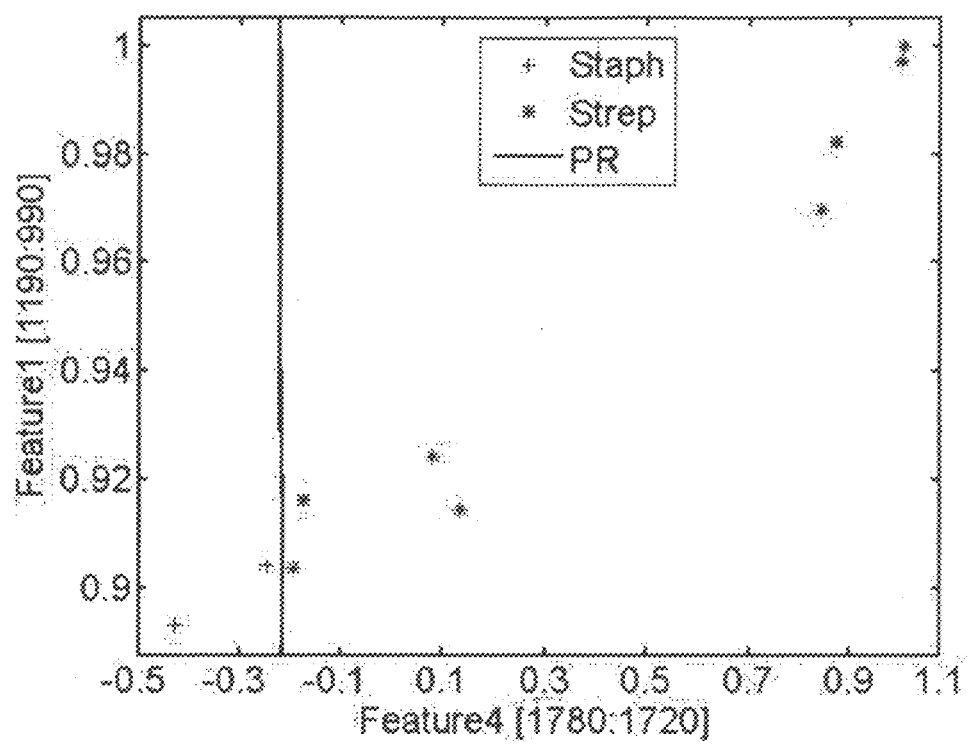

FIG. 36 schematically illustrates the boundaries of a two dimensions area that identifies the bacteria within a solution.

DETAILED DESCRIPTION OF THE PREFERRED EMBODIMENTS

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide means and methods for detecting bacteria within a sample by using Spectroscopic measurements.

Spectroscopic measurements, whether absorption fluorescence Raman, and scattering are the bases for all optical sensing devices. In order to identify a hazardous material (for example a bacteria) a sample that might contain the material is placed inside a spectrometer and the absorption spectrum of the sample is then analyzed to verify whether the spectral signature of the hazardous material is recognized.

The present invention provides means and methods for detection or identification of bacteria by analyzing the absorption spectra of a sample which might contain bacteria.

The term "sample" refers herein to either an aerosol sample or a liquid sample. The present invention provides detection means that enable the detection of bacteria in liquids as well as in aerosol. The detection means can be used for medical or non-medical applications. Furthermore, the detection means can be used, for example, in detecting bacteria in water, beverages, food production, sensing for hazardous materials in crowded places etc.

The term "Pearson's correlation coefficient" refers hereinafter to the correlation between two variables that reflects the degree to which the variables are related. Pearson's correlation reflects the degree of linear relationship between two variables. It ranges from +1 to −1. A correlation of −1 means that there is a perfect negative linear relationship between variables. A correlation of 0 means there is no linear relationship between the two variables. A correlation of 1 means there is a complete linear relationship between the two variables.

A commonly used formula for computing Pearson's correlation coefficient r is the following one:

$$r = \frac{\sum XY - \frac{\sum X \sum Y}{N}}{\sqrt{\left(\sum X^2 - \frac{(\sum X)^2}{N}\right)\left(\sum Y^2 - \frac{(\sum Y)^2}{N}\right)}}$$

The term "about" refers hereinafter to a range of 25% below or above the referred value.

The term "segments" refers hereinafter to wavelength ranges within the absorption spectrum.

The term "n dimensional volume" refers hereinafter to a volume in an n dimensional space that is especially adapted to identify the bacteria under consideration. The n dimensional volume is constructed by extracting features and statistical correlations from the absorption spectrum or its derivatives.

The term "n dimensional space" refers hereinafter to a space where each coordinate is a feature or a statistical correlation extracted from the bacteria spectral signature or a calculated statistical correlation calculated out of the spectrum and its derivatives or from a segment of the spectrum and/or its derivatives.

The term "n dimensional volume boundaries" refers hereinafter to a range that includes about 95% of the bacteria under consideration possible features and correlation values.

Methods and means for bacteria detection adapted to utilize the unique spectroscopic signature of microbes/bacteria/hazardous materials and thus enables the detection of the microbes/bacteria/hazardous materials within a sample are provided by the present invention.

Figure 1:
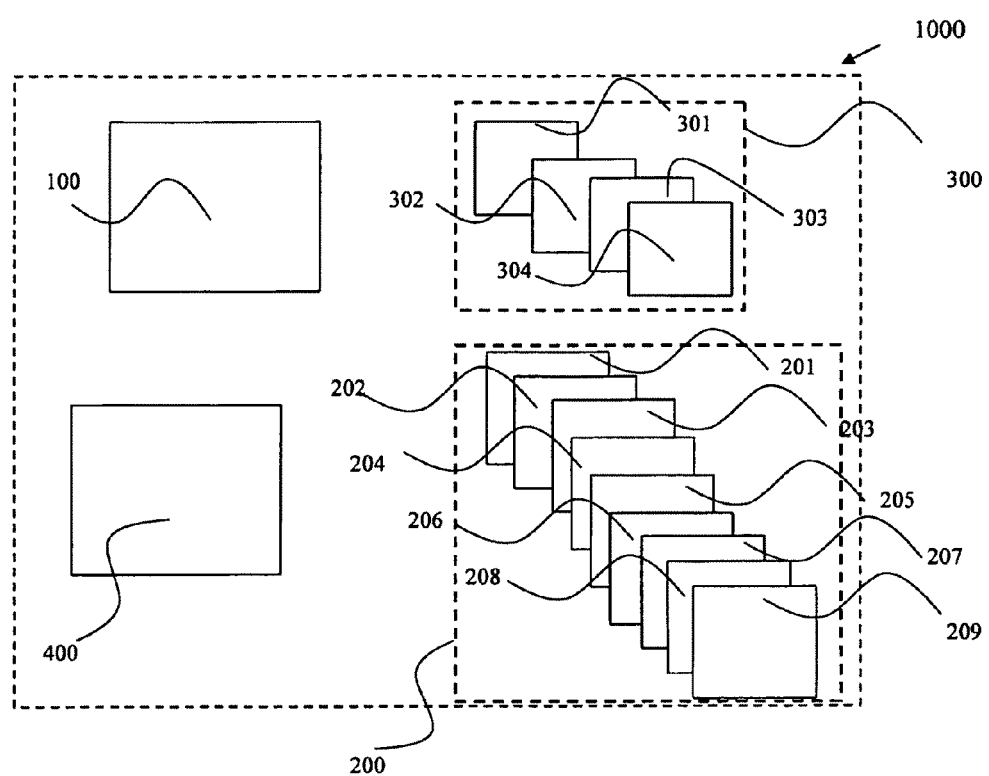
FIGS. 1-2 illustrate a system 1000 and 2000 adapted to detect and/or identify bacteria within a sample according to preferred embodiments of the present invention.

Reference is now made to FIG. 1, illustrating a system 1000 adapted to detect and/or identify specific bacteria within a sample according to one preferred embodiment of the present invention. System 1000 comprises:
  a. means 100 for obtaining an absorption spectrum (AS) of the sample;
  b. statistical processing means 200 for acquiring the n dimensional volume boundaries for the specific bacteria, having:
    i. means 201 for obtaining at least one absorption spectrum (AS2) of samples containing the specific bacteria;
    ii. means 202 for extracting x features from the AS2 selected from a group consisting of peaks wavelength, peaks height and widths, different peaks' intensity ratios or any combination thereof; x is an integer higher or equal to one;
    iii. means 203 for calculating at least one derivative of the AS2;
    iv. means 204 for dividing the AS2 into several segments according to the x features;
    v. means 205 for calculating the y statistical correlation of each of the segment; y is an integer higher or equal to one;
    vi. means 206 for defining n dimensional space; n equals the sum of the x features and they statistical correlations;
    vii. means 207 for assigning each of the x feature and the y correlation to the specific bacteria;
    viii. means 208 for calculating the Gaussian distribution for each of the x feature and/or for each of the y statistical correlations; the Gaussian distributions defined the n dimensional volume in the n dimensional space;
    ix. means 209 for determining the boundaries of the n dimensional volume by using technique selected from a group consisting of quadratic Gaussian classifier, k nearest neighbor, Bayesian classification or any combination thereof;

c. means 300 for data processing the AS, having:
  i. means 301 for noise reducing by using different smoothing techniques selected from a group consisting of running average savitzky-golay or any combination thereof;
  ii. means 302 for extracting m features from the AS selected from a group consisting of peak's width, intensity, the ratio width/intensity, peak's wavelength, different peaks' intensity ratios, or any combination thereof; m is an integer higher or equal to one;
  iii. means 303 for dividing the AS into several segments according to the m features;
  iv. means 304 for calculating the $m_1$ statistical correlation of each of the segment; $m_1$ is an integer higher or equal to one; and, d. means 400 for detecting and/or identifying the specific bacteria if the $m_1$ statistical correlation and/or the m features are within the n dimensional volume.

According to another embodiment of the present invention, means 300 (in system 1000) for data processing the AS additionally characterized by:
  i. means 305 for calculating at least one of the $o^{th}$ derivative of the AS; o is an integer greater than or equals 1;
  ii. means 306 for extracting $m_2$ features from the $o^{th}$ derivative selected from a group consisting of peak's width, intensity, the ratio width/intensity, different peaks' intensity ratios, peak's wavelength or any combination thereof;
  iii. means 307 for dividing the $o^{th}$ derivative into several segments according to the $m_2$ features;
  iv. means 308 for calculating the $m_3$ statistical correlation in each of the segments; and,
  v. means 309 for detecting and/or identifying the specific bacteria if the $m_1$ and/or $m_3$ statistical correlation and/or the m and/or the $m_2$ features are within the n dimensional volume.

According to another embodiment of the present invention, means 308 or 304 (in system 1000) for calculating the statistical correlation is selected from a group consisting of Pearson's correlation coefficient.

According to yet another embodiment of the present invention, the specific bacteria to be identified by system 1000 is selected from a group consisting of *Streptococcus Pyogenes*, Group C and G beta-hemolytic streptococci, *Corynebacterium haemolyticum*, Diphtheria and Ulcerans, *Neisseria Gonorrhoeae, Mycoplasma Pneumoniae, Yersinia Enterocolitica, Mycobacterium tuberculosis, Chlamydia Trachomatiss* and *Pneumoniae, Bordetella Pertussis, Legionella* spp, *Pneumocystis Carinii, Nocardia, Histoplasma Capsulatum, Coccidioides Immitis, Haemophilus influenza* group A beta hemolytic and *staphylococcus Aureus*.

According to another embodiment of the present invention, the means 100 for obtaining an absorption spectrum (AS) of the sample (in system 1000), additionally comprising:
  a. at least one optical cell for accommodating the sample;
  b. p light source selected from a group consisting of laser, lamp, LEDs tunable lasers, monochrimator, p is an integer equal or greater than 1; the p light source are adapted to emit light at different wavelength to the optical cell; and,
  c. detecting means for receiving the spectroscopic data of the sample exiting from the optical cell.

According to yet another embodiment of the present invention, the p light source (in system 1000) are adapted to emit light at wavelength range selected from a group consisting of UV, visible, IR, mid-IR, far-IR and terahertz.

Figure 2:
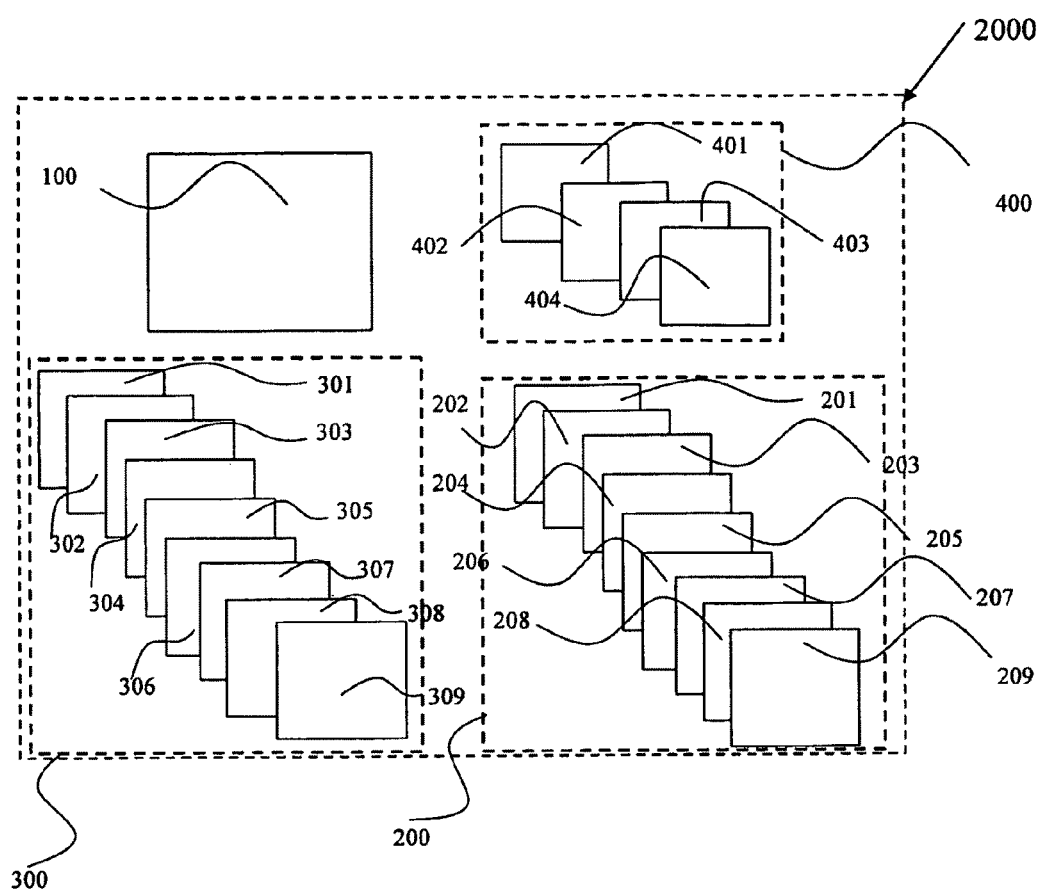

Reference is now made to FIG. 2, illustrating a system 2000 adapted to detect and/or identify specific bacteria within a sample, according to another preferred embodiment of the present invention. System 2000 comprises:
a. means 100 for obtaining an absorption spectrum (AS) of the sample; the AS containing water influence;
b. statistical processing means 200 for acquiring the n dimensional volume boundaries for the specific bacteria, having:
  i. means 201 for obtaining at least one absorption spectrum (AS2) of samples containing the specific bacteria;
  ii. means 202 for extracting x features from the AS2 selected from a group consisting of peaks wavelength, peaks height and widths, different peaks' intensity ratios or any combination thereof; x is an integer higher or equal to one;
  iii. means 203 for calculating at least one derivative of the AS2;
  iv. means 204 for dividing the AS2 into several segments according to the x features;
  v. means 205 for calculating the y statistical correlation of each of the segment; y is an integer higher or equal to one;
  vi. means 206 for defining n dimensional space; n equals the sum of the x features and the y statistical correlations;
  vii. means 207 for assigning each of the x feature and the y correlation to the specific bacteria;
  viii. means 208 for calculating the Gaussian distribution for each of the x feature and/or for each of the y statistical correlations; the Gaussian distributions defined the n dimensional volume in the n dimensional space;
  ix. means 209 for determining the boundaries of the n dimensional volume by using technique selected from a group consisting of quadratic Gaussian classifier, k nearest neighbor, Bayesian classification or any combination thereof;
c. means 300 for eliminating the water influence from said AS, comprising:
  i. means 301 for providing the absorption intensity at each of wavenumber $\tilde{v}$ within said AS ($Sig_{with\ water}(\tilde{v})$);
  ii. means 302 for dividing said AS into at least two wavenumber ranges;
  iii. means 303 for calculating the correction factors (CF) at each wavenumber $\tilde{v}$ within said least two ranges ($CF(\tilde{v})$);
  iv. means 304 for acquiring from said AS at least one absorption intensity that is mainly influenced by water $Sig_{water\ only}(\tilde{v}_q)$ and the corresponding wavenumbers ($\tilde{v}_q$);
  v. means 305 for calculating at least one correction factor of said water ($CF_{water\ only}(\tilde{v}_q)$) at said at least one wavenumber ($\tilde{v}_q$);
  vi. means 306 for dividing said at least one $Sig_{water\ only}(\tilde{v}_q)$ by said at least one $CF_{water}$ ($Sig_{water\ only}(\tilde{v}_q)/CF_{water\ only}(\tilde{v}_q)$) at said at least one wavenumber $\tilde{v}_q$;
  vii. means 307 for calculating the average of step (vi) ($AVG[Sig_{water\ only}(\tilde{v}_q)/CF_{water\ only}(\tilde{v}_q)]$);

viii. means 308 for multiplying said AVG[$Sig_{water\ only}(\tilde{v}_q)/CF_{water\ only}(\tilde{v}_q)$] by said $CF(\tilde{v})$ for each of said wavenumber $\tilde{v}$ within said AS; and, ix. means 309 for subtracting the result of step (viii) from said ($Sig_{with\ water}(\tilde{v})$) at each of said wavenumber $\tilde{v}$ within said AS;

d. means 400 for data processing the AS without the water influence, characterized by:

i. means 401 for noise reducing by using different smoothing techniques selected from a group consisting of running average savitzky-golay or any combination thereof;

ii. means 402 for extracting m features from the AS selected from a group consisting of peak's width, intensity, the ratio width/intensity, peak's wavelength, different peaks' intensity ratios, or any combination thereof; m is an integer higher or equal to one;

iii. means 403 for dividing the AS into several segments according to the m features;

iv. means 404 for calculating the $m_1$ statistical correlation of each of the segment; $m_1$ is an integer higher or equal to one; and, e. means 500 for detecting and/or identifying the specific bacteria if the $m_1$ statistical correlation and/or the m features are within the n dimensional volume.

According to another embodiment of the present invention, means 400 (in system 2000) for data processing the AS without the water influence additionally comprising:

i. means 405 for calculating at least one of the $o^{th}$ derivative of the AS; o is an integer greater than or equals 1;

ii. means 406 for extracting $m_2$ features from the $o^{th}$ derivative selected from a group consisting peak's width, intensity, the ratio width/intensity, different peaks' intensity ratios, peak's wavelength or any combination thereof;

iii. means 407 for dividing the $o^{th}$ derivative into several segments according to the $m_2$ features;

iv. means 408 for calculating the $m_3$ statistical correlation in each of the segments; and, v. means 409 for detecting and/or identifying the specific bacteria if the $m_1$ and/or $m_3$ statistical correlation and/or the m and/or the $m_2$ features are within the n dimensional volume.

According to another embodiment of the present invention, means 408 and/or 404 within system 2000, for calculating the statistical correlation in each of said segments is selected form a group consisting of Pearson's correlation coefficient.

According to another embodiment of the present invention, the specific bacteria (in system 2000) is selected from a group consisting of *Streptococcus Pyogenes*, Group C and G beta-hemolytic streptococci, *Corynebacterium haemolyticum*, Diphtheria and Ulcerans, *Neisseria Gonorrhoeae, Mycoplasma Pneumoniae, Yersinia Enterocolitica, Mycobacterium tuberculosis, Chlamydia Trachomatiss* and *Pneumoniae, Bordetella Pertussis, Legionella* spp, *Pneumocystis Carinii, Nocardia, Histoplasma Capsulatum, Coccidioides Immitis, Haemophilus influenza* group A beta hemolytic and *staphylococcus Aureus*.

According to another embodiment of the present invention, means 100 for obtaining an absorption spectrum (AS) of the sample additionally comprising:

a. at least one optical cell for accommodating the sample;

b. p light source selected from a group consisting of laser, lamp, LEDs tunable lasers, monochrimator, p is an integer equal or greater than 1; p light source are adapted to emit light at different wavelength to the optical cell; and, c. detecting means for receiving the spectroscopic data of the sample exiting from the optical cell.

According to yet another embodiment of the present invention, the p light source are adapted to emit light at wavelength range selected from a group consisting of UV, visible, IR, mid-IR, far-IR and terahertz.

Yet another object of the present invention is to provide a method for detecting and/or identifying specific bacteria within a sample. The method comprises step selected inter alia from:

a. obtaining an absorption spectrum (AS) of the sample;

b. acquiring the n dimensional volume boundaries for the specific bacteria by:

i. obtaining at least one absorption spectrum (AS2) of samples containing the specific bacteria;

ii. extracting x features from the AS2 selected from a group consisting of peaks wavelength, peaks height and widths, different peaks' intensity ratios or any combination thereof; x is an integer higher or equal to one;

iii. calculating at least one derivative of the AS2;

iv. dividing the AS2 into several segments according to the x features;

v. calculating the y statistical correlation of each of the segment; y is an integer higher or equal to one;

vi. defining n dimensional space; n equals the sum of the x features and they statistical correlations;

vii. assigning each of the x feature and the y correlation to the specific bacteria;

viii. calculating the Gaussian distribution for each of the x feature and/or for each of the y statistical correlations; the Gaussian distributions defined the n dimensional volume in the n dimensional space;

ix. determining the boundaries of the n dimensional volume by using technique selected from a group consisting of quadratic Gaussian classifier, k nearest neighbor, Bayesian classification or any combination thereof.

c. data processing the AS;

i. noise reducing by using different smoothing techniques selected from a group consisting of running average savitzky-golay or any combination thereof;

ii. extracting m features from the AS selected from a group consisting of peak's width, intensity, the ratio width/intensity, peak's wavelength, different peaks' intensity ratios, or any combination thereof; m is an integer higher or equal to one;

iii. dividing the AS into several segments according to the m features;

iv. calculating the $m_1$ statistical correlation of each of the segment; $m_1$ is an integer higher or equal to one; and, d. detecting and/or identifying the specific bacteria if the $m_1$ statistical correlation and/or the m features are within the n dimensional volume.

It should be pointed out that in each of the systems as described above (either 1000 or 2000), the statistical processing means 200 is used only once for each specific bacteria. Once the boundaries were provided by the statistical processing means 200 the determination whether the specific bacteria is present in a sample is performed by verifying whether the $m_1$ and/or $m_3$ statistical correlation and/or the m and/or $m_2$ features are within the boundaries. Furthermore, once the boundaries were provided, there exists no need for the statistical processing of the same specific bacteria again.

Yet another object of the present invention is to provide a method for detecting and/or identifying specific bacteria within a sample. The method comprises steps selected inter alia from:

a. obtaining an absorption spectrum (AS) of the sample; the AS containing water influence;
b. acquiring the n dimensional volume boundaries for the specific bacteria by:
   i. obtaining at least one absorption spectrum (AS2) of samples containing the specific bacteria;
   ii. extracting x features from the AS2 selected from a group consisting of peaks wavelength, peaks height and widths, different peaks' intensity ratios or any combination thereof; x is an integer higher or equal to one;
   iii. calculating at least one derivative of the AS2;
   iv. dividing the AS2 into several segments according to the x features;
   v. calculating the y statistical correlation of each of the segment; y is an integer higher or equal to one;
   vi. defining n dimensional space; n equals the sum of the x features and they statistical correlations;
   vii. assigning each of the x feature and the y correlation to the specific bacteria;
   viii. calculating the Gaussian distribution for each of the x feature and/or for each of the y statistical correlations; the Gaussian distributions defined the n dimensional volume in the n dimensional space;
   ix. determining the boundaries of the n dimensional volume by using technique selected from a group consisting of quadratic Gaussian classifier, k nearest neighbor, Bayesian classification or any combination thereof;
c. eliminating the water influence from the AS by:
   i. providing the absorption intensity at each of wavenumber (x) within said AS ($Sig_{with\ water}(\tilde{v})$);
   ii. dividing said AS into at least two wavenumber ranges;
   iii. calculating the correction factors (CF) at each wavenumber $\tilde{v}$ within said least two ranges ($CF(\tilde{v})$);
   iv. acquiring from said AS at least one absorption intensity that is mainly influenced by said water $Sig_{water\ only}(\tilde{v}_q)$ and the corresponding wavenumbers ($\tilde{v}_q$);
   v. calculating at least one correction factor of said water ($CF_{water\ only}(\tilde{v}_q)$) at said at least one wavenumber ($\tilde{v}_q$);
   vi. dividing said at least one $Sig_{water\ only}(\tilde{v}_q)$ by said at least one $CF_{water}(Sig_{water\ only}(\tilde{v}_q)/CF_{water\ only}(\tilde{v}_q))$ at said at least one wavenumber $\tilde{v}_q$;
   vii. calculating the average of step (vi) (AVG $[Sig_{water\ only}(\tilde{v}_q)/CF_{water\ only}(\tilde{v}_q)]$);
   viii. multiplying said $AVG[Sig_{water\ only}(\tilde{v}_q)/CF_{water\ only}(\tilde{v}_q)]$ by said $CF(\tilde{v})$ for each of said wavenumber $\tilde{v}$ within said AS; and,
   ix. subtracting the result of step (viii) from said ($Sig_{with\ water}(\tilde{v})$) at each of said wavenumber $\tilde{v}$ within said AS;
d. data processing the AS without the water influence by:
   i. noise reducing by using different smoothing techniques selected from a group consisting of running average savitzky-golay or any combination thereof;
   ii. extracting m features from the AS selected from a group consisting of peak's width, intensity, the ratio width/intensity, peak's wavelength, different peaks' intensity ratios, or any combination thereof; m is an integer higher or equal to one;
   iii. dividing the AS into several segments according to the m features;
   iv. calculating the $m_1$ statistical correlation of each of the segment; $m_1$ is an integer higher or equal to one; and,
e. detecting and/or identifying the specific bacteria if the $m_1$ statistical correlation and/or the m features are within the n dimensional volume.

In each of the methods as described above, the statistical processing is used only once for each specific bacteria. Once the boundaries were provided by the statistical processing the determination whether the specific bacteria is present in a sample is performed by, verifying whether the $m_1$ statistical correlation and/or said m features are within the boundaries. Furthermore, once the boundaries were provided, there exists no need for the statistical processing of the same specific bacteria again. According to another embodiment of the present invention step (c) of data processing the AS, in the methods as described above, additionally comprising steps of:

i. calculating at least one of the $o^{th}$ derivative of the AS; o is an integer greater than or equals 1;
ii. extracting $m_2$ features from the $o^{th}$ derivative selected from a group consisting of peak's width, intensity, the ratio width/intensity, different peaks' intensity ratios, peak's wavelength or any combination thereof;
iii. dividing the $o^{th}$ derivative into several segments according to the $m_2$ features;
iv. calculating the $m_3$ statistical correlation in each of the segments; and,
v. detecting and/or identifying the specific bacteria if the $m_1$ and/or $m_3$ statistical correlation and/or the m and/or the $m_2$ features are within the n dimensional volume.

According to another embodiment of the present invention, the step of calculating the statistical correlation of each of said segment, in the methods as described above, is performed by using Pearson's correlation coefficient.

According to another embodiment of the present invention, the methods as described above, additionally comprising the step of selecting the specific bacteria selected from a group consisting of *Streptococcus Pyogenes*, Group C and G beta-hemolytic streptococci, *Corynebacterium haemolyticum*, Diphtheria and Ulcerans, *Neisseria Gonorrhoeae*, *Mycoplasma Pneumoniae*, *Yersinia Enterocolitica*, *Mycobacterium tuberculosis*, *Chlamydia Trachomatiss* and *Pneumoniae*, *Bordetella Pertussis*, *Legionella* spp, *Pneumocystis Carinii*, *Nocardia*, *Histoplasma Capsulatum*, *Coccidioides Immitis*, *Haemophilus influenza* group A beta hemolytic and *staphylococcus Aureus*.

According to another embodiment of the present invention, the step of obtaining the AS, in the methods as described above, additionally comprising the following steps:

a. providing at least one optical cell accommodates the sample;
b. providing p light source selected from a group consisting of laser, lamp, LEDs tunable lasers, monochrimator, p is an integer equal or greater than 1; p light source are adapted to emit light to the optical cell;
c. providing detecting means for receiving the spectroscopic data of the sample;
d. emitting light from the light source at different wavelength to the optical cell; and,
e. collecting the light exiting from the optical cell by the detecting means; thereby obtaining the AS.

According to another embodiment of the present invention, the step of emitting light is performed at the wavelength range of UV, visible, IR, mid-IR, far-IR and terahertz.

According to another embodiment of the present invention, the methods as defined above, additionally comprising the step of detecting the bacteria by analyzing the AS in the region of about 3000-3300 cm$^{-1}$ and/or about 850-1000 cm$^{-1}$ and/or about 1300-1350 cm$^{-1}$.

According to yet another embodiment of the present invention, the absorption spectra, in any of the systems (1000 or 2000) or for any of the methods as described above, is obtained using an instrument selected from the group consisting of a Fourier transform infrared spectrometer, a fluorometer and a Raman spectrometer.

According to yet another embodiment of the present invention, the uncultured sample, in any of the systems (1000 or 2000) or for any of the methods as described above, is selected from fluid originated from the human body such as blood, saliva, urine, bile, vaginal secretions, middle ear aspirate, pus, pleural effusions, synovial fluid, abscesses, cavity swabs, and serum.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

EXAMPLES

Examples are given in order to prove the embodiments claimed in the present invention. The examples describe the manner and process of the present invention and set forth the best mode contemplated by the inventors for carrying out the invention, but are not to be construed as limiting the invention.

Example 1

Water Influence

One of the major problems in identifying bacteria from a fluid sample's spectrum (and especially an aerosol, spectrum) is the water influence (i.e., the water noise which masks the desired spectrum by the water spectrum).

The water molecule may vibrate in a number of ways. In the gas state, the vibrations involve combinations of symmetric stretch (v1), asymmetric stretch (v3) and bending (v2) of the covalent bonds. The water molecule has a very small moment of inertia on rotation which gives rise to rich combined vibrational-rotational spectra in the vapor containing tens of thousands to millions of absorption lines. The water molecule has three vibrational modes x, y and z. The following table (table 1) illustrates the water vibrations, wavelength and the assignment of each vibration:

TABLE 1 water vibrations, wavelength and the assignment of each vibration

| Wavelength | cm-1 | Assignment |
|---|---|---|
| 0.2 mm | 50 | intermolecular bend |
| 55 μm | 183.4 | intermolecular stretch |
| 25 μm | 395.5 | L1, librations |
| 15 μm | 686.3 | L2, librations |
| 6.08 μm | 1645 | v2, bend |
| 4.65 μm | 2150 | v2 + L2 b |
| 3.05 μm | 3277 | v1, symmetric stretch |
| 2.87 μm | 3490 | v3, asymmetric stretch |
| 1900 nm | 5260 | av1 + v2 + bv3; a + b = 1 |
| 1470 nm | 6800 | av1 + bv3; a + b = 2 |
| 1200 nm | 8330 | av1 + v2 + bv3; a + b = 2 |
| 970 nm | 10310 | av1 + bv3; a + b = 3 |
| 836 nm | 11960 | av1 + v2 + bv3; a + b = 3 |
| 739 nm | 13530 | av1 + bv3; a + b = 4 |
| 660 nm | 15150 | av1 + v2 + bv3; a + b = 4 |
| 606 nm | 16500 | av1 + bv3; a + b = 5 |
| 514 nm | 19460 | av1 + bv3; a + b = 6 | a and b are integers, ≥0 ms.

The present invention provides a method for significantly reducing and even eliminating the water influence within the absorption spectra.

Figure 3:
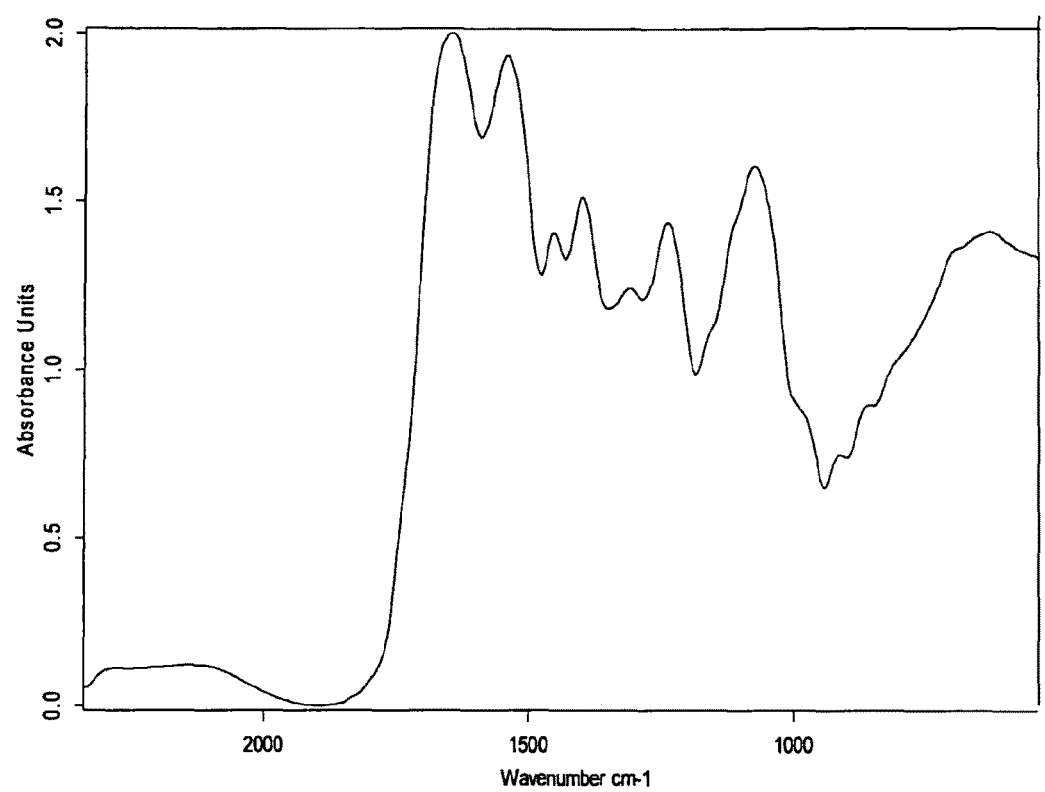
FIGS. 3-4 illustrate an absorption spectrum prior to the water correction (FIG. 3) and after the water correction (FIG. 4).
Figure 4:
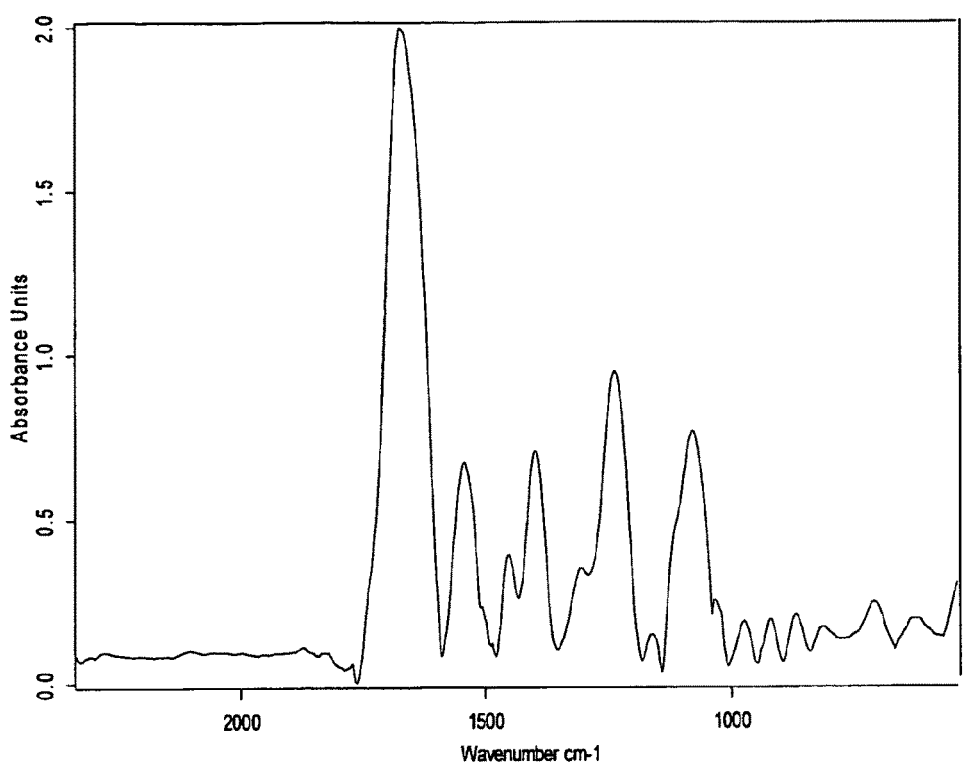

Reference is now made to FIGS. 3 and 4 which illustrate an absorption spectrum of a sample with and without the water influence. Example for a spectrum without the water influence is given in FIG. 4. FIG. 3 represents a spectrum prior to the water correction.

The method for eliminating the water influence contains the following steps:

First the absorption spectrum was divided in several segments (i.e, wavelength ranges). The spectrum was divided to segments (wavenumber ranges) of about 1800 cm$^{-1}$ to about 2650 cm$^{-1}$, about 1400 cm$^{-1}$ to about 1850 cm$^{-1}$, about 1100 cm$^{-1}$ to about 1450 cm$^{-1}$, about 950 cm$^{-1}$ to about 1100 cm$^{-1}$, about 550 cm$^{-1}$ to about 970 cm$^{-1}$.

The segments were determined according to (i) different intensity peaks within the water's absorption spectrum; and, (ii) the signal's trends.

Next, each segment was eliminated from the water influence in the following manner:

(a) providing the absorption intensity at each of wavenumber $\tilde{v}$ within the absorption spectrum (referred hereinafter as $Sig_{with\ water}(\tilde{v})$);

(b) calculating the correction factors (CF) at each wavelength (refers hereinafter as x) within each segment (referred hereinafter as $CF(\tilde{v})$);

(c) acquiring from the absorption spectrum, at least one absorption intensity that is mainly influenced by water (referred hereinafter as $Sig_{water\ only}(\tilde{v}_q)$) at the corresponding wavenumbers $\tilde{v}_q$;

(d) calculating at least one correction factor of the water ($CF_{water\ only}(\tilde{v}_q)$) at said at least one wavenumber $\tilde{v}_q$;

(e) dividing at least one $Sig_{water\ only}(\tilde{v}_q)$ by at least one $CF_{water}(Sig_{water\ only}(\tilde{v}_q)/CF_{water\ only}(\tilde{v}_q))$ at said at least one wavenumber $\tilde{v}_q$;

(f) calculating the average of the results of step (e) (referred hereinafter as $AVG[Sig_{water\ only}(\tilde{v}_q)/CF_{water\ only}(\tilde{v}_q)]$;

(g) multiplying the $AVG[Sig_{water\ only}(\tilde{v}_q)/CF_{water\ only}(\tilde{v}_q)]$ by $CF(\tilde{v})$ for each wavenumber $\tilde{v}$; and, (h) Subtracting each result of step (g) from $Sig_{with\ water}(\tilde{v})$ for each $\tilde{v}$.

In other words, each absorption intensity within the spectrum is eliminated from the water influence according to the following equation:

$$Sig_{with\ water}(\tilde{v}) - (CF(\tilde{v}) * AVG[Sig_{water\ only}(\tilde{v}_q) / CF_{water\ only}(\tilde{v}_q)])$$

Calculating the Correction Factors

The correction factors (CF) depends on the wavelength range, the water absorption peak's shape at each wavelength, peak's width, peak's height, absorption spectrum trends and any combination thereof. The following series were used as a correction factor (x—denote the wavenumber in $cm^{-1}$)

1. Wavelength range 1846 $cm^{-1}$ to 2613 $cm^{-1}$
Coefficients:
a11=137.2;
b11=2170;
c11=224.3;
a21=19.02;
b21=2063;
c21=37.53;
a31=0.7427;
b31=2224;
c31=13;
a41=98.33;
b41=2124;
c41=109.8;
a51=−4.988;
b51=2192;
c51=33.87;
a61=20.19;
b61=1998;
c61=40.22;
a71=228.3;
b71=1496;
c71=1329;
a81=6.751e+012;
b81=−1226;
c81=592.1;

$$CF(x) = a11 * e^{(-((x-b11)/c11)^2)} + a21 * e^{(-((x-b21)/c21)^2)} + a31 * e^{(-((x-b31)/c31)^2)} + a41 * e^{(-((x-b41)/c41)^2)} + a51 * e^{(-((x-b51)/c51)^2)} + a61 * e^{(-((x-b61)/c61)^2)} + a71 * e^{(-((x-b71)/c71)^2)} + a81 * e^{(-((x-b81)/c81)^2)}$$

2. Wavelength range 1461 $cm^{-1}$ to 1846 $cm^{-1}$
a12=−300.2;
b12=1650;
c12=13.65;
a22=−51.65;
b22=1665;
c22=6.48;
a32=142.4;
b32=1623;
c32=7.584;
a42=1450;
b42=1649;
c42=32.62;
a52=96.34;
b52=1617;
c52=2.387;
a62=608;
b62=1470;
c62=369.3;
a72=0;
b72=1873;
c72=2.625;
a82=1037;
b82=1644;
c82=76.21;

$$CF(x) = a12 * e^{(-((x-b12)/c21)^2)} + a22 * e^{(-((x-b22)/c22)^2)} + a32 * e^{(-((x-b32)/c32)^2)} + a42 * e^{(-((x-b42)/c42)^2)} + a52 * e^{(-((x-b52)/c52)^2)} + a62 * e^{(-((x-b62)/c62)^2)} a72 * e^{(-((x-b72)/c72)^2)} + a82 * e^{(-((x-b82)/c82)^2)}$$

3. Wavelength range 1111 $cm^{-1}$ to 1461 $cm^{-1}$
a13=1368;
b13=2167;
c13=767;
a23=80.67;
b23=1356;
c23=68.83;
a33=36.85;
b33=1307;
c33=33.79;
a43=142.5;
b43=1244;
c43=67.19;
a53=260.4;
b53=1130;
c53=88.91;
a63=66.54;
b63=1093;
c63=31;
a73=7.126;
b73=1345;
c73=20.9;
a83=4.897;
b83=1280;
c83=11.05;

$$CF(x) = a13 * e^{(-((x-b13)/c13)^2)} + a23 * e^{(-((x-b23)/c23)^2)} + a33 * e^{(-((x-b33)/c33)^2)} + a43 * e^{(-((x-b43)/c43)^2)} + a53 * e^{(-((x-b53)/c53)^2)} + a63 * e^{(-((x-b63)/c63)^2)} + a73 * e^{(-((x-b73)/c73)^2)} + a83 * e^{(-((x-b83)/c83)^2)}$$

4. Wavelength range 961 $cm^{-1}$ to 1111 $cm^{-1}$
a14=692.6;
b14=952;
c14=31.04;
a24=48.46;
b24=983.2;
c24=15.72;
a34=287.5;
b34=994.6;
c34=27.98;
a44=434.9;
b44=1032;
c44=40.86;
a54=17.05;
b54=1052;
c54=13.55;
a64=48.61;
b64=1068;
c64=16.56;
a74=70.71;
b74=1086;
c74=21.23;
a84=497.3;
b84=1124;
c84=64.42;

$$CF(x) = a14 * e^{(-((x-b14)/c14)^2)} + a24 * e^{(-((x-b24)/c24)^2)} + a34 * e^{(-((x-b34)/c34)^2)} + a44 * e^{(-((x-b44)/c44)^2)} + a54 * e^{(-((x-b54)/c54)^2)} + a64 * e^{(-((x-b64)/c64)^2)} + a74 * e^{(-((x-b74)/c74)^2)} + a84 * e^{(-((x-b84)/c84)^2)}$$

Wavelength range 570 $cm^{-1}$ to 961 $cm^{-1}$
a15=−2877;
b15=36.23;
c15=29.09;

a25=0;
b25=−124.3;
c25=22.09;
a35=−190.7;
b35=18.97;
c35=16.45;
a45=1.589e+004;
b45=−3.427;
c45=56.25;
a55=−1.352e+004;
b55=−5.861;
c55=40.75;
a65=476.7;
b65=82.38;
c65=17.29;
a75=1286;
b75=62.29;
c75=180.3;
a85=802.9;
b85=102.8;
c85=18.79;

$$CF(x) = a15 * e^{(-((x-b15)/c15)^2)} + a25 * e^{(-((x-b25)/c25)^2)} + a35 * e^{(-((x-b35)/c35)^2)} + a45 * e^{(-((x-b45)/c45)^2)} + a55 * e^{(-((x-b55)/c55)^2)} + a65 * e^{(-((x-b65)/c65)^2)} + a75 * e^{(-((x-b75)/c75)^2)} + a85 * e^{(-((x-b85)/c85)^2)}$$

Absorption Intensity Mainly Influenced by Water

Reference is made again to FIG. 3 which illustrate the absorption spectrum prior to eliminating the water influence.

As can be seen from the figure, the absorption intensity that is mainly influenced by the water is the wavenumber region of 2000 cm$^{-1}$ and above. The intensity at that region is about 0.2 absorption units. In the present example, $\tilde{v}_q$ is 2000 and $Sig_{water\ only}(\tilde{v}_q)$ is 0.2.

Reference is made again to FIG. 4, which illustrate the absorption spectrum of a sample after the influence of the water was eliminated.

It should be pointed out that for the purpose of obtaining a better resolution both graphs (3 and 4) are normalized to 2 (i.e., multiplied by 2).

Example 2

Bacteria's Absorption Spectrum

Each type of bacteria has a unique spectral signature. Although many types of bacteria have similar spectral signatures there are still some spectral differences that are due to different proteins on the cell membrane and differences in the DNA/RNA structure. The following table, table 2, lists the wavelengths in the IR region that can be used to identify a bacterium.

TABLE 2 bacterium wavelengths in the IR region

| Wavelength [nm] | Wavenumber [cm$^{-1}$] | Assignment |
|---|---|---|
| 2857 | 3500 | O—H stretch etch of hydroxyl groups |
| 3125 | 3200 | N—H stretch (amide A) of proteins |
| 3379 | 2959 | C—H stretch (asymmetric) of —CH3 |
| 3408 | 2934 | C—H stretch (asymmetric) of >CH2 |
| 3423 | 2921 | C—H stretch (asymmetric) of >CH2 in fatty acids |
| 3450 | 2898 | C—H stretch of C—H methine |
| 3481 | 2872 | C—H stretch (symmetric) of CH3 |
| 3506 | 2852 | C—H stretch (symmetric) of >CH2 in fatty acids |
| 5743 | 1741 | >C═O stretch of esters |
| 5830 | 1715 | >C═O stretch of esters, RNA/DNA, OH—C═O |
| 5899 | 1695 | Amide I band components |
| 5934 | 1685 | resulting from antiparallel |
| 5970 | 1675 | pleated sheets and b-turns of proteins |
| 6042 | 1655 | Amide I of a-helical stretch uctures |
| 6108 | 1637 | Amide I of b-pleated sheet stretch uctures |
| 6459 | 1548 | Amide II |
| 6600 | 1515 | "Tyrosine" band |
| 6811 | 1468 | C—H def of >CH2 |
| 7142 | 1400 | C═O stretch (symmetric) of COO$^-$ |
| 7633-8064 | 1310-1240 | Amide III band components of proteins |
| 8000-8190 | 1250-1220 | P═O stretch (asymmetric) of >PO$_2^-$ hosphodiesters |
| 8333-11111 | 1200-900 | C—O—C, C—O dominated by ring vibrations of carbohydrates C—O—P, P—O—P |
| 9216 | 1085 | P═O stretch (symmetric) of >PO$_2^-$ |
| 13888 | 720 | C—H rocking of >CH$_2$ |
| 11111-16666 | 900-600 | Specific bacteria bonds |

The table was taken from Naumann D., "Infrared spectroscopy in microbiology", *Encyclopedia of Analytical Chemistry*, R. A. Meyers (Ed.) pp. 102-131, John Wiley & Sons Ltd, Chichester, 2000.

Figure 5:
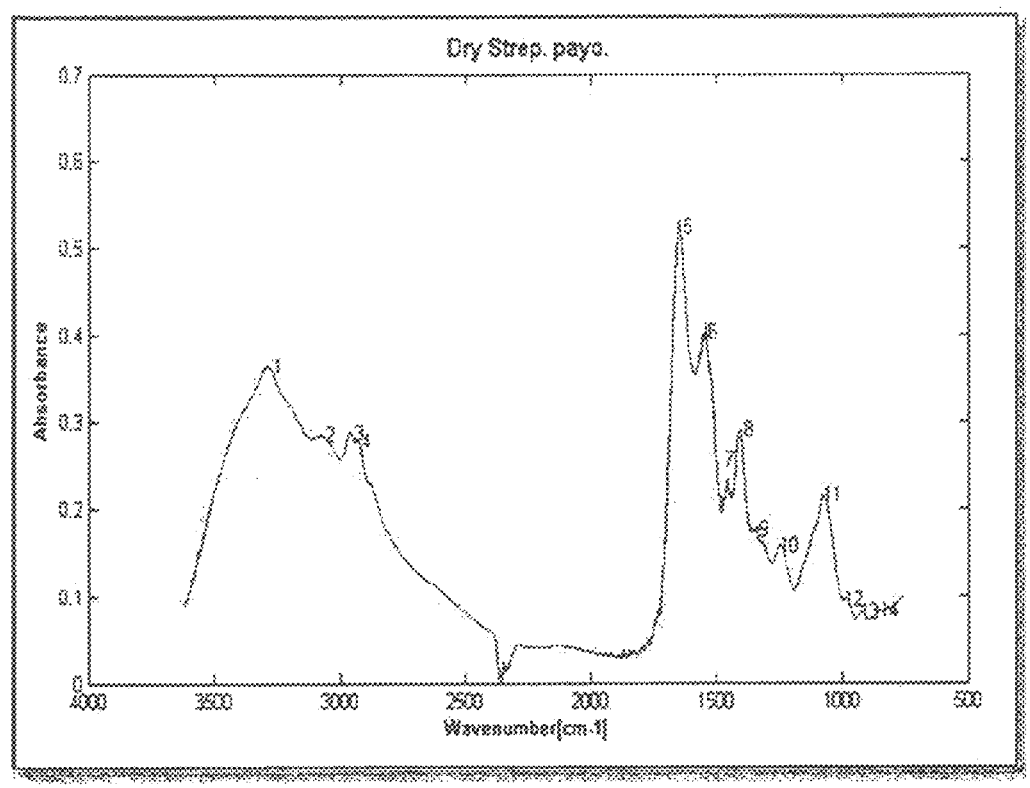
FIG. 5 is an example of the absorption peaks of *streptococcus*.

The following table, table 3, and FIG. 5 is an example of the absorption peaks of *streptococcus payogenous*. Some of the peaks could be related to the peaks in table 2. Others, such as peak number 1, 2, 9, 12, 13 and 14 are specific *streptococcus payogenous* peaks discovered in the present invention and are used for the detection and identification.

TABLE 3

*streptococcus*' absorption peaks

| Peak number | Wavenumber [cm$^{-1}$] | Absorbance | Weighting factor | Assignment |
|---|---|---|---|---|
| 1 | 3286 | 0.3638 | 0.09 | Specific bacteria characteristics |
| 2 | 3077 | 0.2852 | 0.1 | Specific bacteria characteristics |
| 3 | 2962 | 0.2875 | 0.1 | C—H stretch (asymmetric) of —CH3 |
| 4 | 2933 | 0.2785 | 0.09 | C—H stretch (asymmetric) of >CH2 |
| 5 | 1648 | 0.5245 | 0.01 | Amide I of a-helical stretch uctures |
| 6 | 1548 | 0.4029 | 0.01 | Amide II |
| 7 | 1452 | 0.2235 | 0.15 | C—H def of >CH2 |
| 8 | 1405 | 0.2920 | 0.15 | C=O stretch (symmetric) of COO$^-$ |
| 9 | 1348 | 0.1763 | 0.15 | Specific bacteria characteristics |
| 10 | 1245 | 0.1589 | 0.15 | P=O stretch (asymmetric) of >PO$_2^-$ |
| 11 | 1076 | 0.2159 | 0.15 | P=O stretch (symmetric) of >PO$_2^-$ |
| 12 | 989 | 0.0957 | 0.05 | Specific bacteria characteristics |
| 13 | 925 | 0.0821 | 0.05 | Specific bacteria characteristics |
| 14 | 850 | 0.0828 | 0.05 | Specific bacteria characteristics |

Example 3

Distinguishing Between Two Bacteria in a Dry Mixture

The following ex-vivo example provides a method to distinguish between two bacteria within a dry mixture of—*Streptococcus payogenes* and *Staphylococcus aureus* and to identify and/or determine whether *Streptococcus* is present within the sample.

Five mixtures of—*Streptococcus payogenes* and *Staphylococcus aureus* were prepared according to the following protocol:

1. The following solutions of Strep. β hemolytic (cat number-ATCC 19615) and *Staphylococcus aureus* (Cat. Number ATCC 25923) were prepared:

| Total volume | Strep Pyogenes CFU/160 μL | Staph Aurous CFU/160 μL |
|---|---|---|
| 60 | 12 | 0 |
| 60 | 9 | 3 |
| 60 | 6 | 6 |
| 60 | 3 | 9 |
| 60 | 0 | 12 |
| Total | 150 μL | 150 μL |

2. 30 μL of each solution was placed on one marked slot on an optical plate (ZnSe). Another slot contained 30 p. 1 ddH$_2$O for reference.

3. The plate was placed in a desiccator (Dessicator 250 mm polypropylene, Yavin Yeda, Israel) in the presence of several petri plates having a desiccant agent (Phosphorus Pentoxide cat #79610 Sigma Aldrich).

4. The desiccator was vacuumed for about 30 minutes.

Then the samples were placed inside a FTIR spectrometer (Bruker) and the spectral response of the samples was acquired (spectral range 4000 cm$^{-1}$ to 400 cm$^{-1}$).

The absorption spectra of each sample were applied with Blackman-Harris 3-term apodization function (see the following equation):

$$w(n) = a_0 - a_1\cos\left(\frac{2\pi n}{N-1}\right) + a_2\cos\left(\frac{4\pi n}{N-1}\right) - a_3\cos\left(\frac{6\pi n}{N-1}\right)$$

$$a_0 = 0.35875; a_1 = 0.48829; a_2 = 0.14128; a_3 = 0.01168$$

In which w(n) is the Blackman-Harris 3-term apodization; n is integer between 0 to N−1; and, N is the range at which the Blackman-Harris 3-term apodization function was applied.

Next, the sample was scanned sufficient number of times (64 scans) in order to reach a signal to noise ratio greater than 3000:1.

The identification and/or detection of specific bacteria was as follows:

(a) the noise in each of the absorption spectra was reduced by using Savitzky-Golay smoothing;

(b) the signal's first derivative was calculated;

(c) m features such as, but not limited to, peaks wavelength, peaks height and widths, peaks height ratio etc. were extracted from the spectra. A total of m features were extracted. m is an integer higher or equals 1;

(d) the signal and/or its first derivative were divided into several regions (segments, i.e., several wavenumber regions) according to said m features;

(e) $m_1$ statistical correlation were calculated for (i) the spectral signal at each region; and for (ii) the signal derivatives at each region. A total of $m_1$ statistical correlations were extracted. $m_1$ is an integer higher or equals 1. The statistical correlation for the each region (the signal's and its derivatives) was calculated by using Pearson's correlation coefficient;

(f) the m features and the $m_1$ statistical correlation were examined and checked whether they are within the n dimensional volume boundaries (which acquired by the statistical processing);

(g) the identification of the specific bacteria was determined as positive if the m features and/or the $m_1$ statistical correlation were within the n dimensional volume boundaries.

Statistical Processing

The statistical processing is especially adapted to provide the n dimensional volume boundaries. For each specific bacterium the statistical processing was performed only once, for obtaining the boundaries. Once the boundaries were provided, the determination whether the specific bacteria is present in a sample was as explained above (i.e., verifying whether the features or correlation are within the boundaries). Furthermore, once the boundaries were provided, there exists no need for the statistical processing of the same specific bacteria again.

The statistical processing for each specific bacterium is performed in the following manner:

(a) obtaining several absorption spectrum (AS2) of samples containing the specific bacteria;
(b) extracting x features such as, but not limited to, peaks wavelength, peaks height and widths, different peaks' intensity ratios etc. were extracted from the spectra. A total of x features. x is an integer higher or equals 1;
(c) calculating the signal's first derivative;
(d) dividing the signal and/or its first derivative into several regions (segments) according to said x features;
(e) Calculating the y correlation for the different segments within the absorption spectrums;
(f) Defining n dimensional space. n equals the sum of the x features and the y statistical correlations;
(g) Assigning and/or interlinking each one of the x feature, and each one of the y correlation to the specific bacteria which its identification is required;
(h) Calculating the Gaussian distribution for (i) each of the x feature; and/or for (ii) each of the y statistical correlations. All the calculated Gaussian distributions constitute an n dimensional volume in the n dimensional space; and,
(i) Determining the boundaries of each volume by using quadratic Gaussian classifier or similar method (for example k nearest neighbor, Bayesian classification et cetera).

If the features and correlation (extracted from the spectrum) are within the n dimensional volume boundaries, the specific bacteria are identified. Otherwise the bacteria are not identified.

Alternatively or additionally, each of the x feature and/or for the y statistical correlations is given a weighting factor. The weighting factor is determined by the examining how each feature or correlation improves the bacteria detection prediction (for example by using maximum likelihood or Bayesian estimation). Once the weighting factor is assigned to each one of the x feature and the y statistical correlations, the boundaries are determined for the features and/or the statistical correlations having the most significant contribution to the bacteria prediction. Alternatively or additionally, the AS2 is smoothed by reducing the noise. The noise reduction is obtained by different smoothing techniques selected from a group consisting of running average savitzky-golay or any combination thereof.

We'll first present an example for the smoothing technique. For that the entire signal and its first derivative prior to and after the noise are presented.

Then will give examples for the deviation of the spectrum. And lastly an example of the boundaries is given. It should be pointed put that for demonstrating purposes the boundaries were calculated according to the features and/or statistical correlations which had the most significant contribution are given for the samples.

Furthermore, the object of the following examples is to identify *streptococcus*.

Smoothing of the Spectrum

Figure 6:
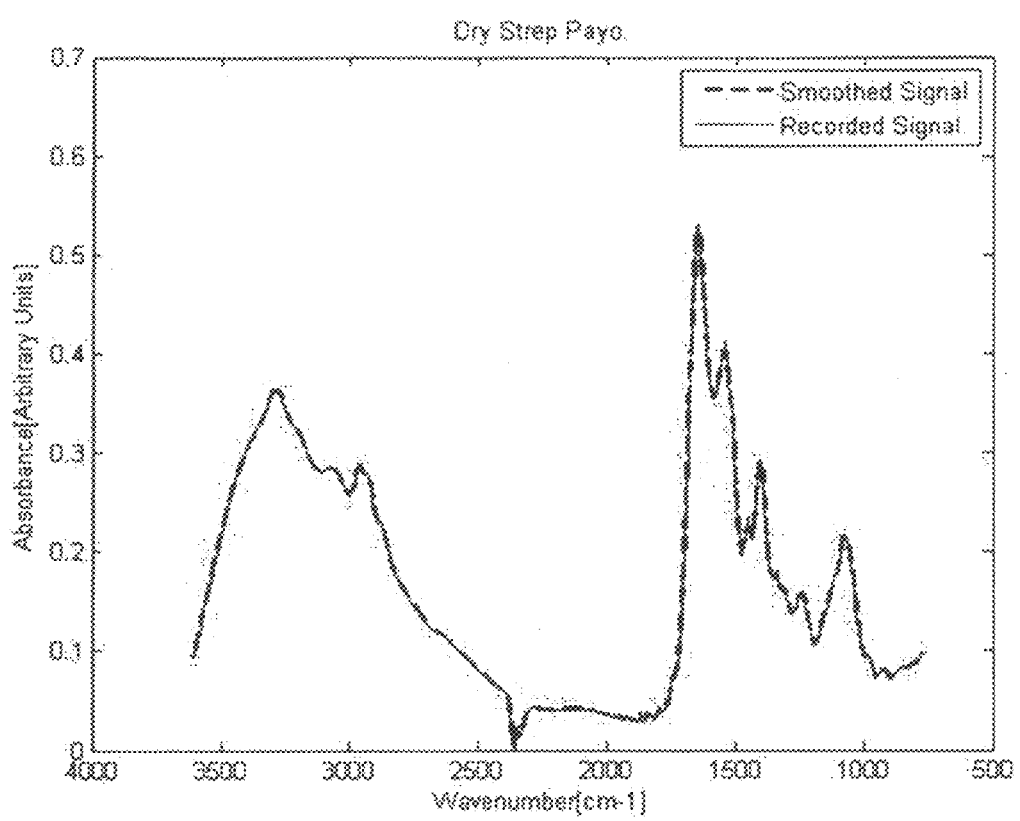
FIG. 6 illustrates the absorption signal of a dry sample containing 100% *streptococcus* prior to and after the noise was reduced.

Reference is now made to FIG. 6 illustrating the absorption signal of a sample containing 100% *streptococcus* prior to and after the noise was reduced (recorded signal vs. smoothed signal).

Figure 7:
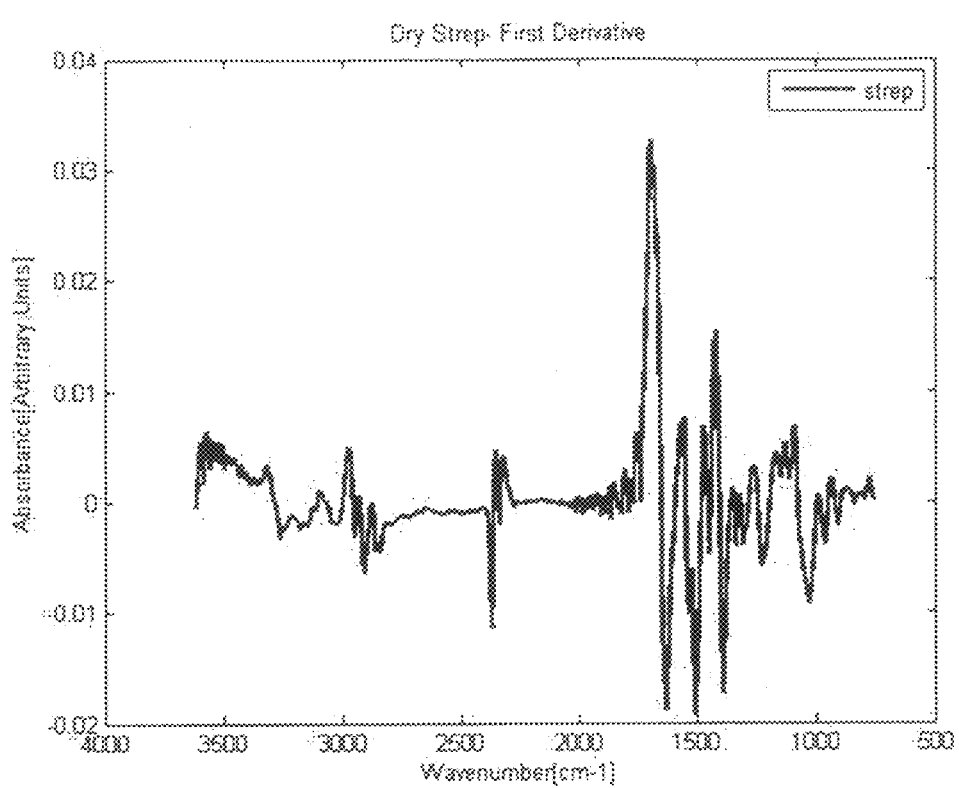
FIG. 7 illustrates the first derivative of the absorption signal in a dry sample containing 100% *streptococcus* prior to and after the noise was reduced.

Reference is now made to FIG. 7 illustrating the signal's first derivative of a sample containing 100% *streptococcus* prior to and after the noise was reduced (recorded signal vs. smoothed signal).

Dividing the Absorption Spectrum and its First Derivative

The absorption spectrum of different samples (having different amount of *streptococcus* and *Staphylococcus*) and the first derivative are given. The absorption spectrum and the first derivative are given as example in two selected segments (950 cm$^{-1}$ to 1200 cm$^{-1}$; and, 1230 cm$^{-1}$ to 1360 cm$^{-1}$).

The entire segments (as divided both for the signal and the first derivative) are listed in table 3 and 4 along with the correlations.

Reference is now made to FIGS. 8-12 which illustrate the absorption spectrum of a sample (solid line) and a reference sample (dotted line) at wavenumber range of 950 cm$^{-1}$ to 1200 cm$^{-1}$ and the corresponding statistical correlation. FIGS. 8-12 also present the first derivative of the spectrum at the same range and the corresponding statistical correlation.

Each of the absorption spectra was smoothed (i.e., noise reduction) by using different techniques (such as running average, Savitzky-Golay etcetera).

Figure 8:
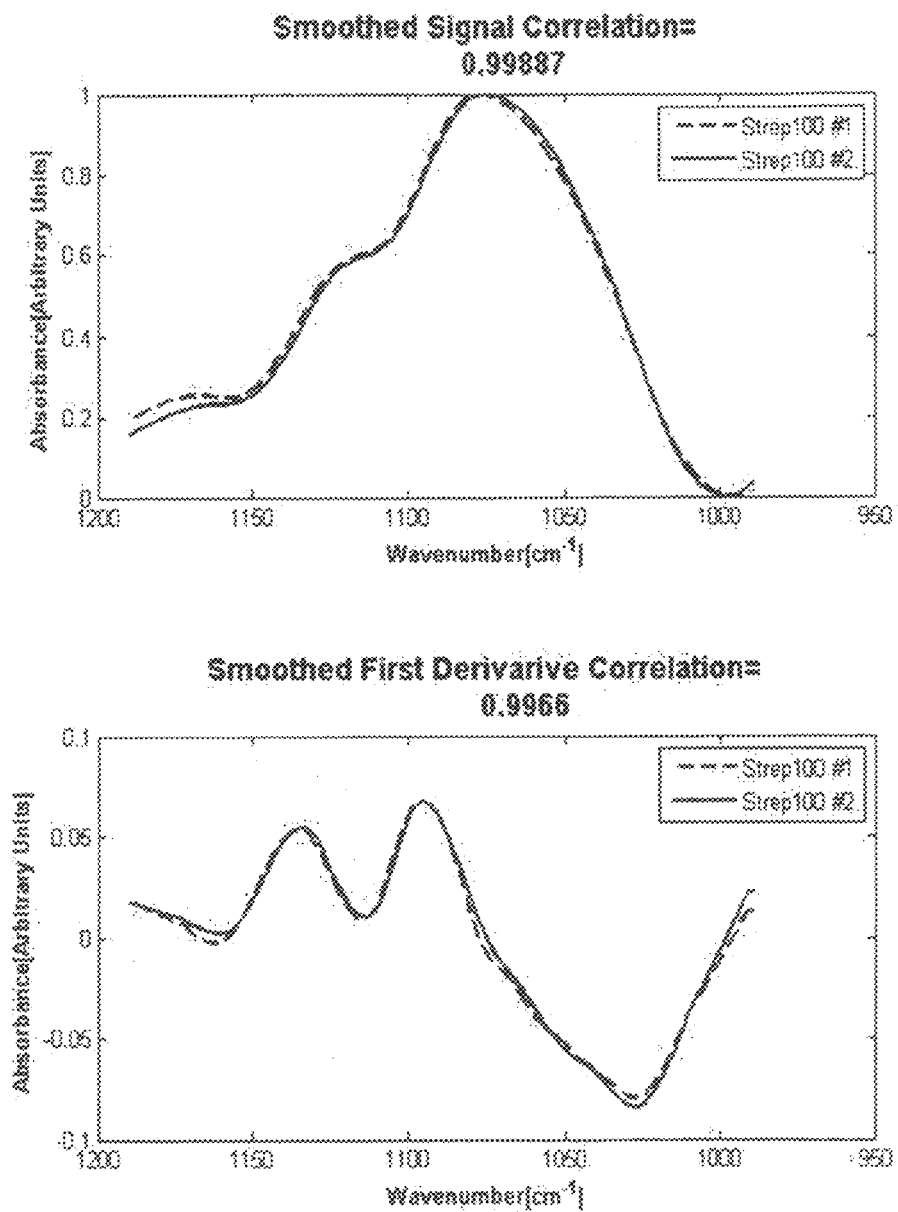
Figure 9:
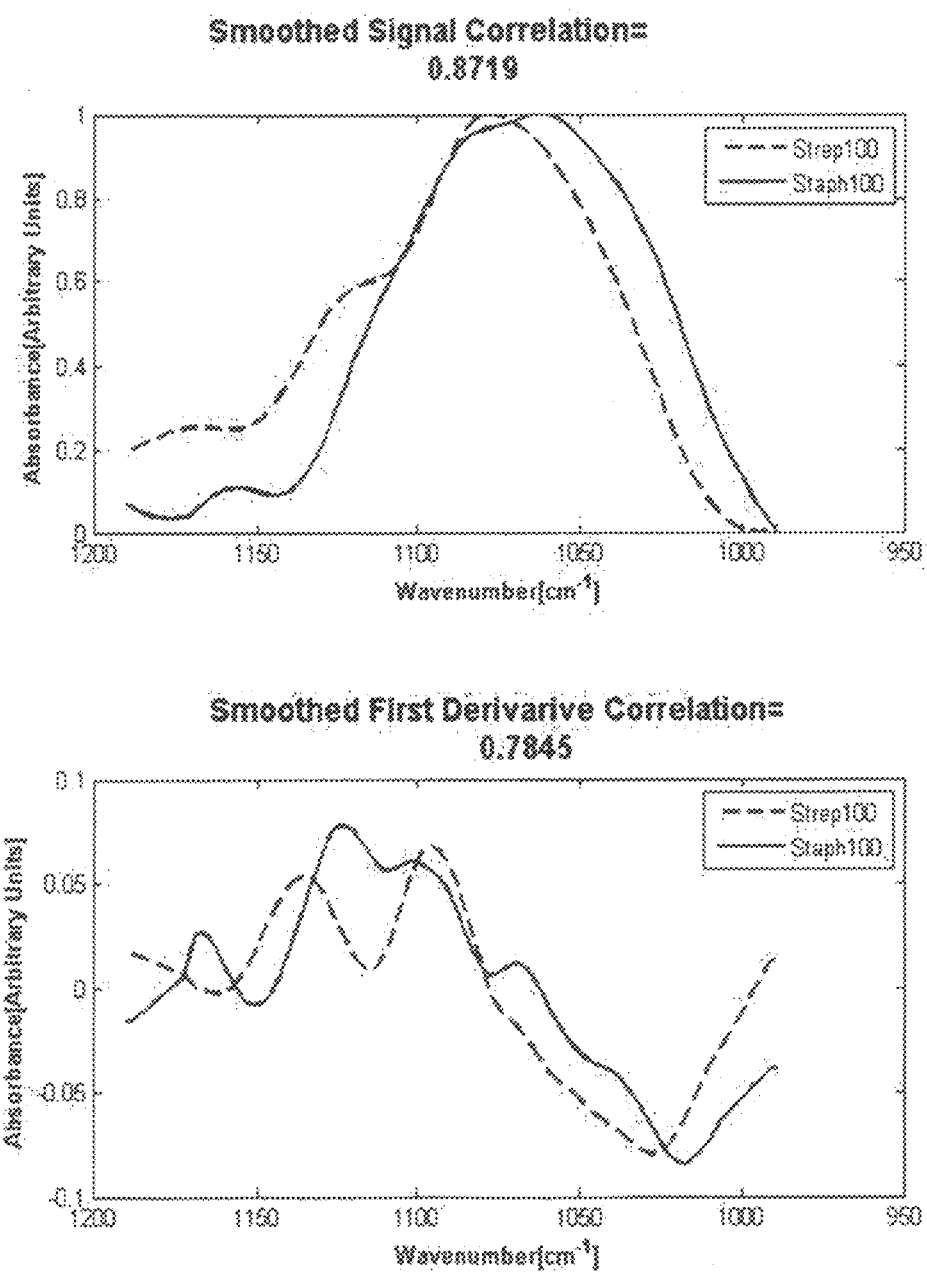
Figure 11:
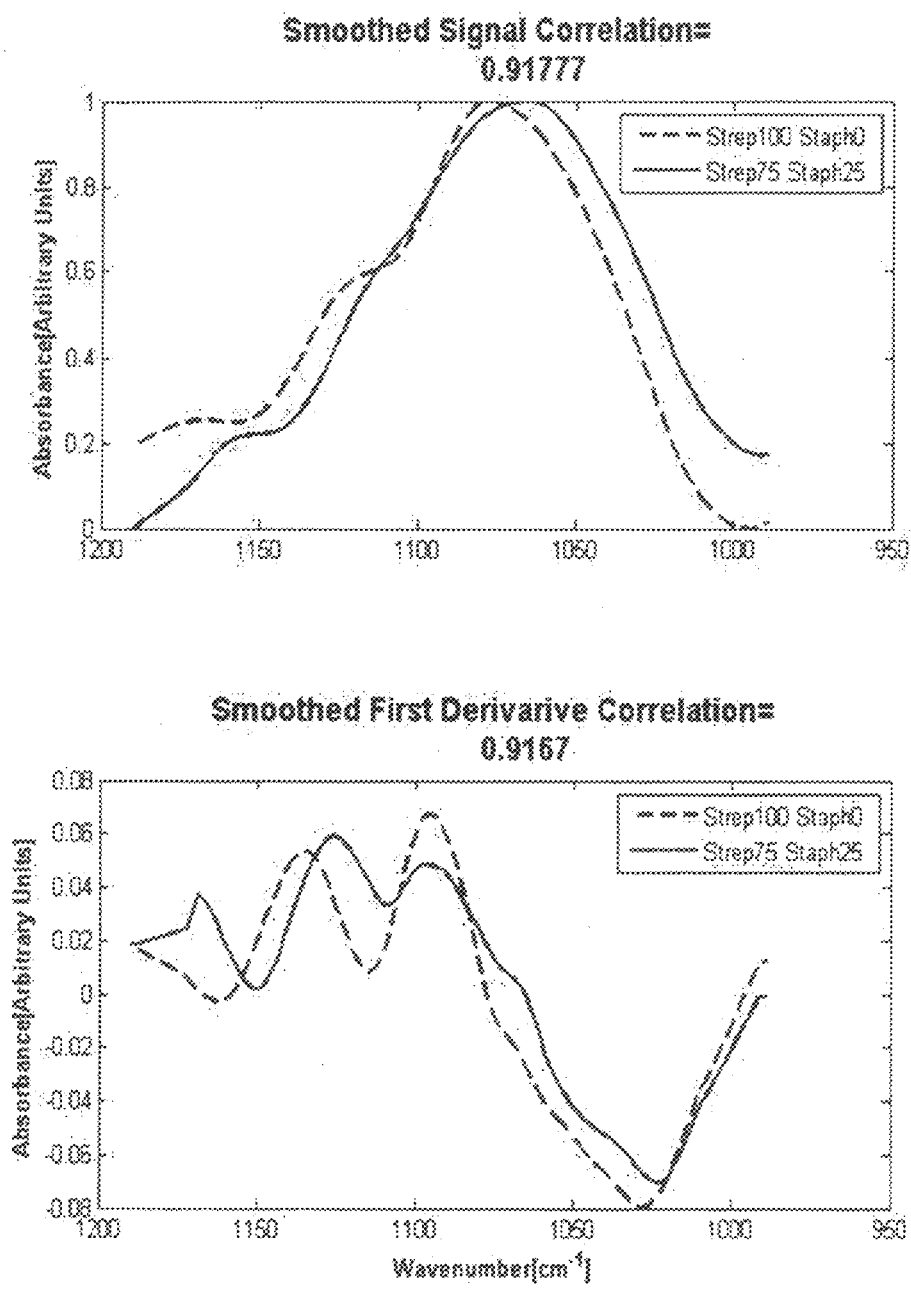
Figure 12:
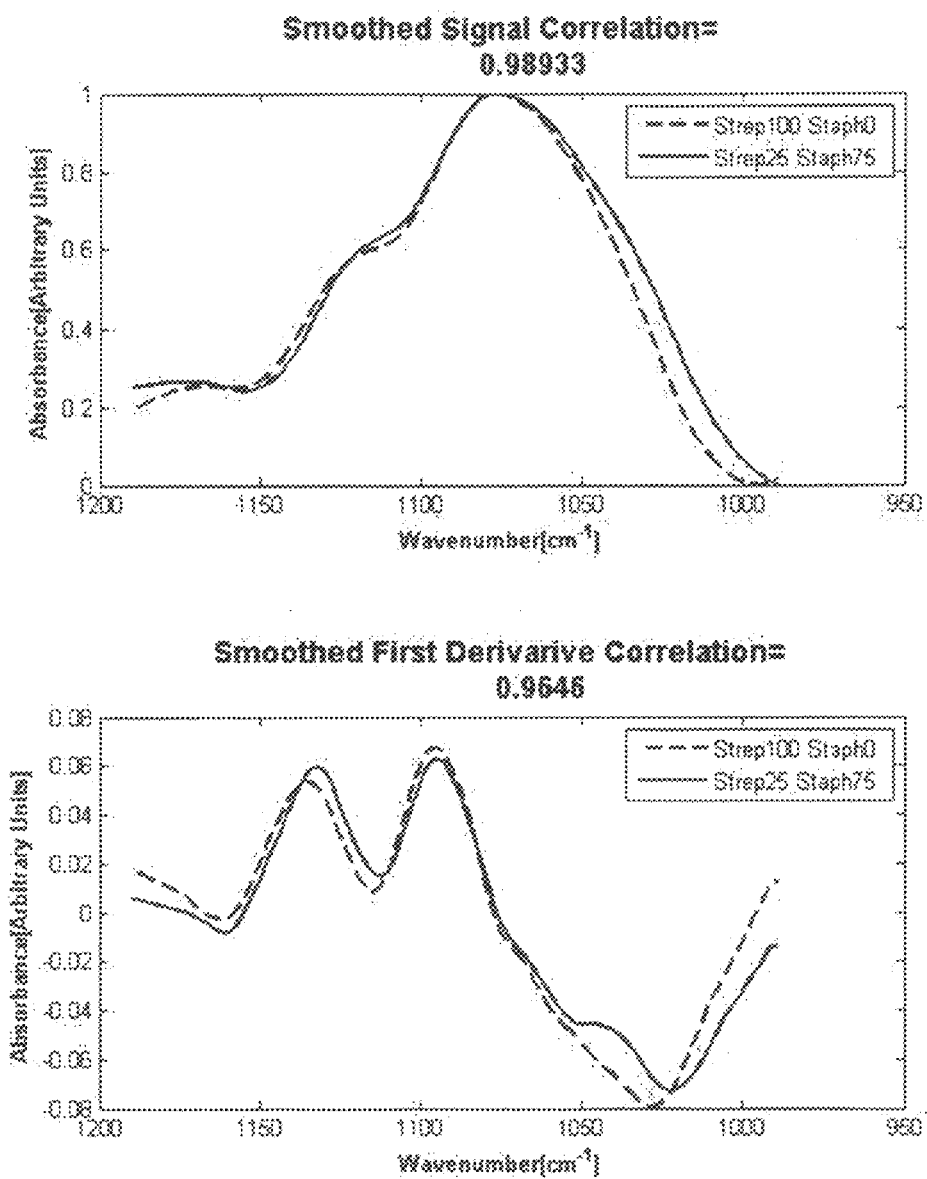

FIG. 8 represents a reference sample having 100% *streptococcus* (dotted line) and a sample having 100% *streptococcus* (solid line);

FIG. 9 represents a reference sample having 100% *streptococcus* (dotted line) and a sample having 100% *Staphylococcus* (solid line);

FIG. 10 represents a reference sample having 100% *streptococcus* (dotted line) and a sample having 50% *streptococcus* and 50% *Staphylococcus* (solid line);

FIG. 11 represents a reference sample having 100% *streptococcus* (dotted line) and a sample having 75% *streptococcus* and 25% *Staphylococcus* (solid line);

FIG. 12 represents a reference sample having 100% *streptococcus* (dotted line) and a sample having 25% *streptococcus* and 75% *Staphylococcus* (solid line).

Reference is now made to FIGS. 13-17 which illustrate the first derivative of an absorption spectrum of a sample (solid line) and a reference sample (dotted line) at wavenumber range of 1220 cm$^{-1}$ to 1380 cm$^{-1}$ and the corresponding statistical correlation. FIGS. 13-17 also present the first derivative of the spectrum at the same range and the corresponding statistical correlation.

Each of the absorption spectra was smoothed (i.e., noise reduction) by using different techniques (such as running average, Savitzky-Golay etcetera).

Figure 15:
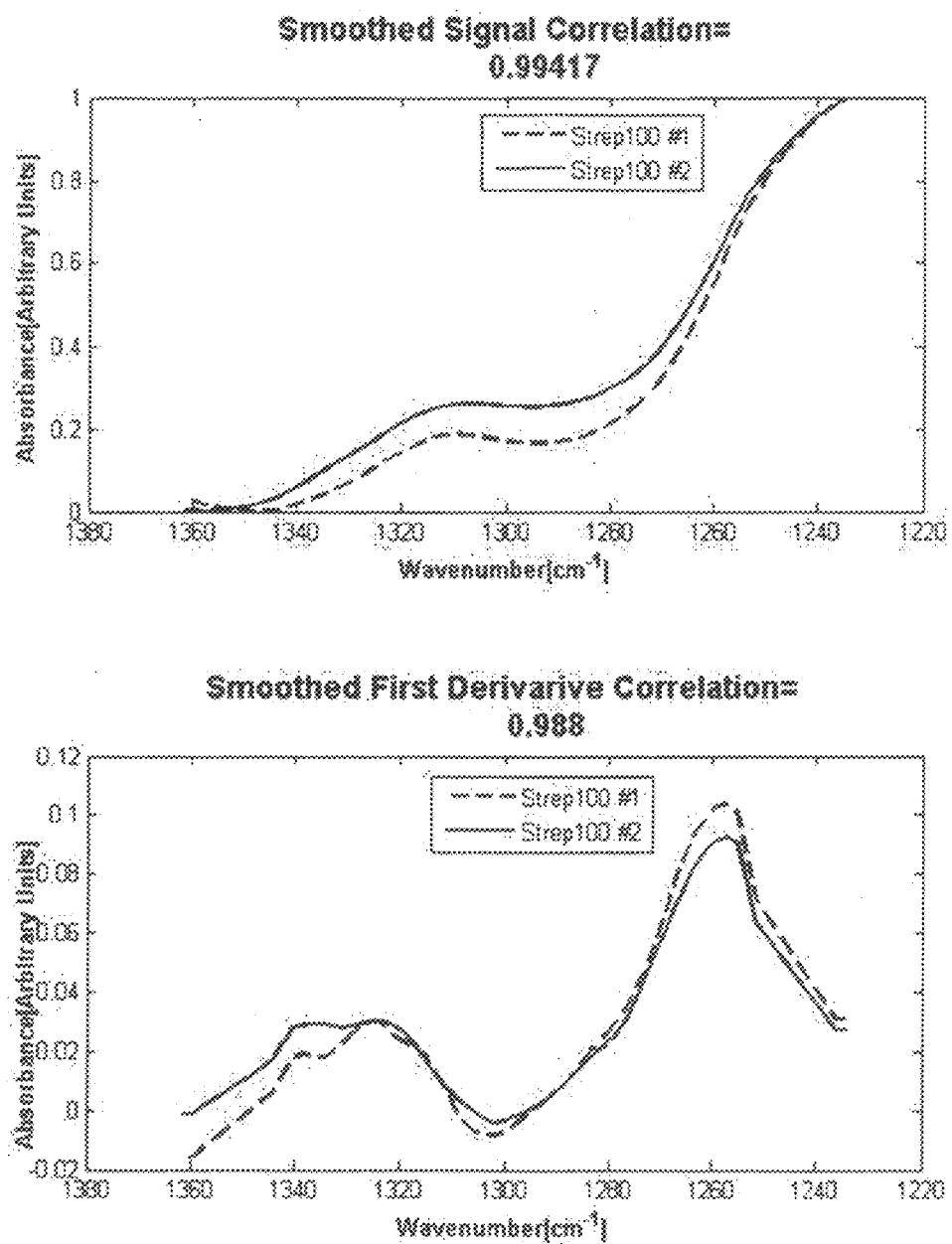
Figure 14:
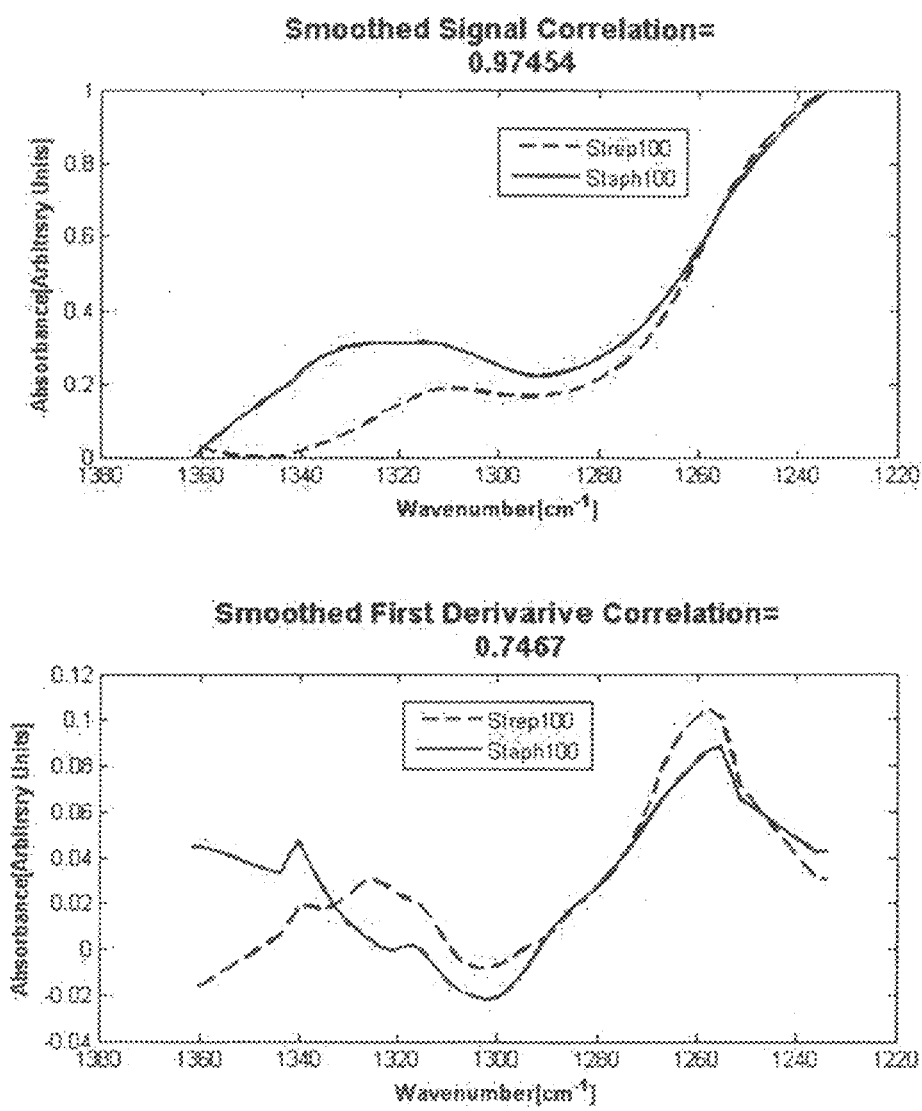
Figure 15:
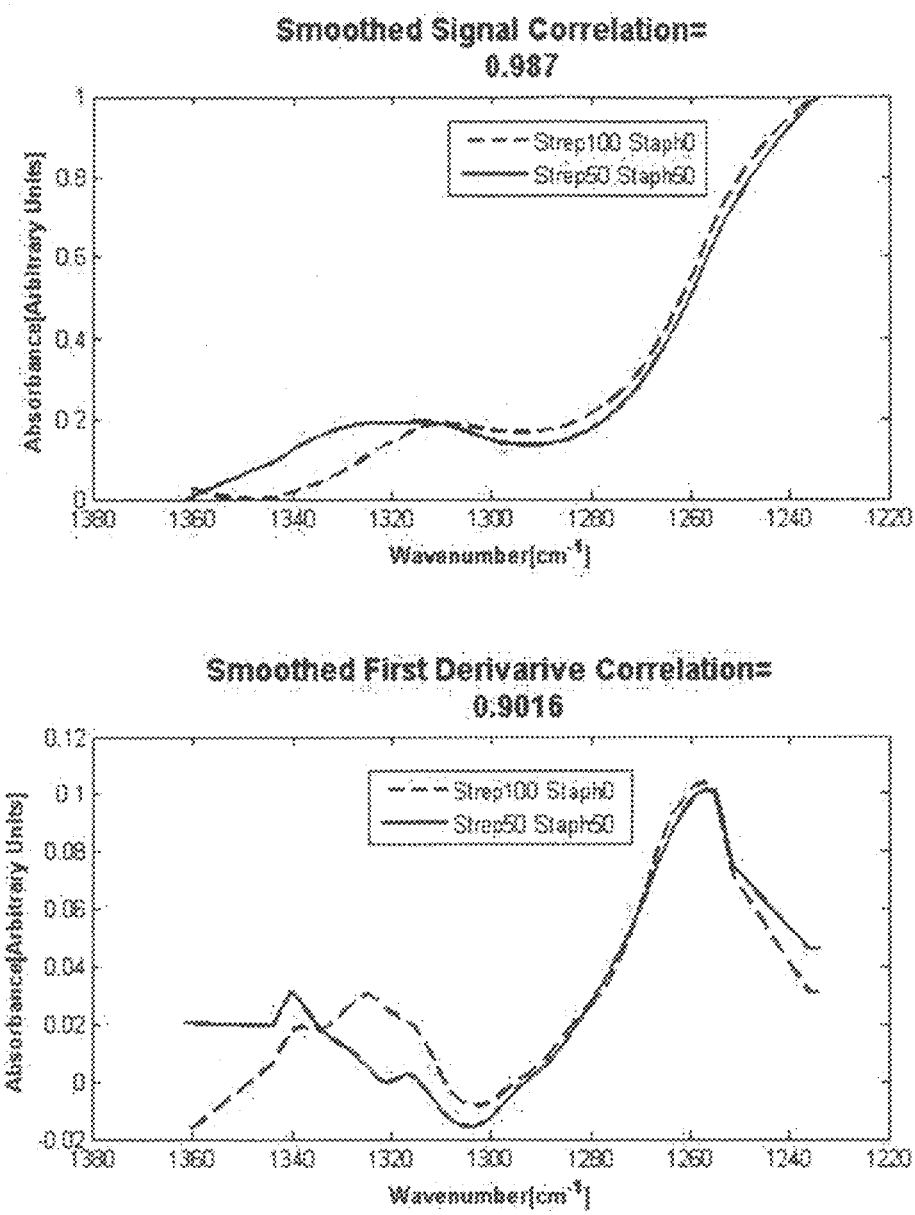
Figure 16:
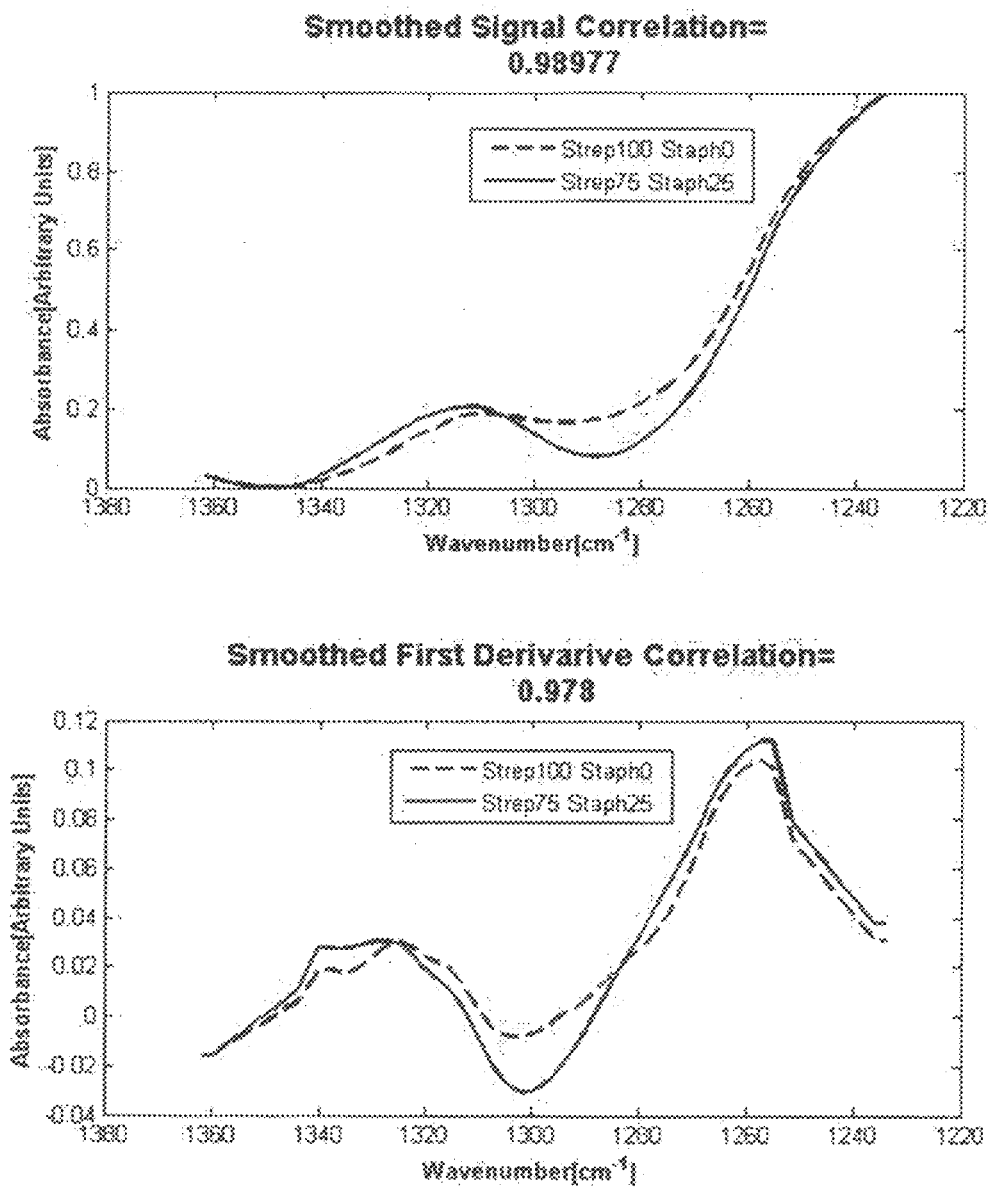
Figure 17:
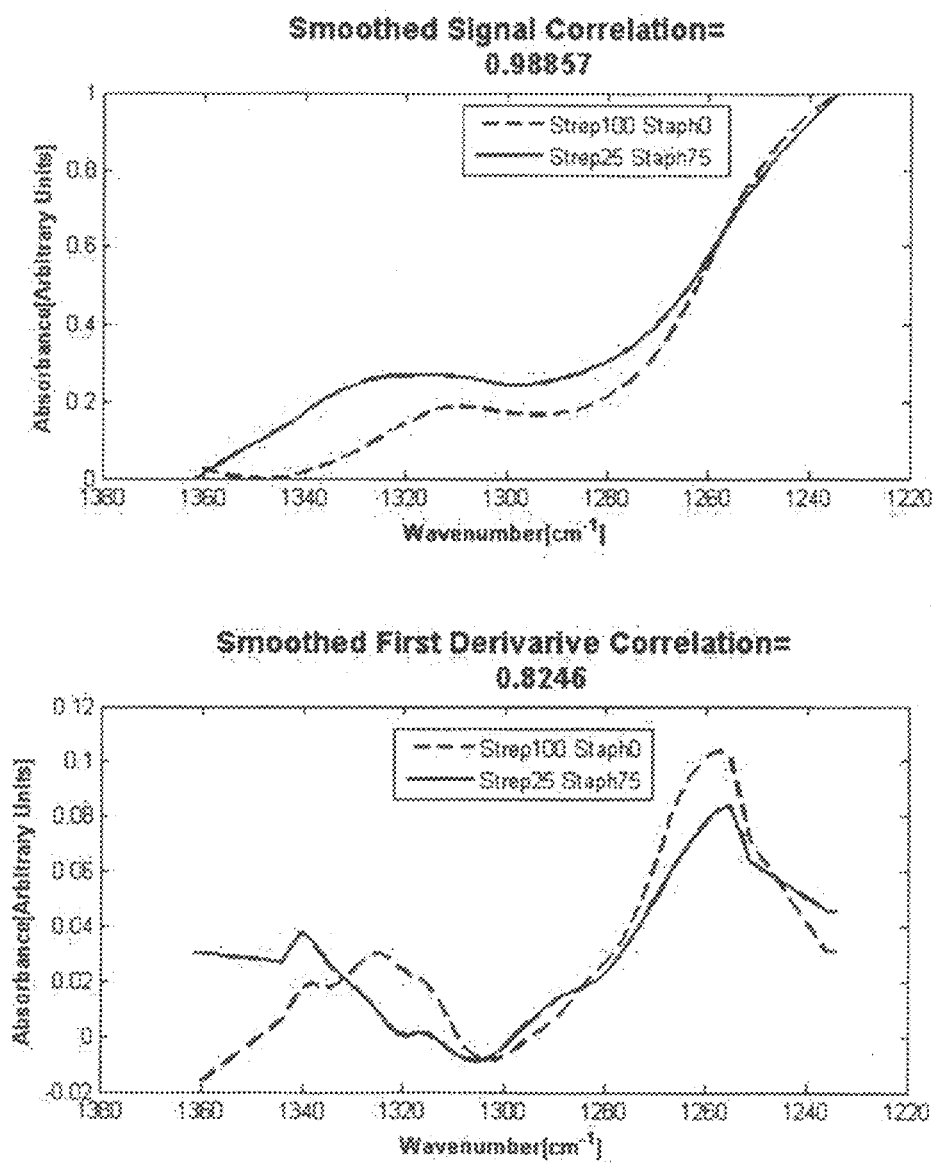

FIG. 13 represents the first derivative of a reference sample having 100% *streptococcus* (dotted line) and the first derivative of a sample having 100% *streptococcus* (solid line);

FIG. 14 represents the first derivative of a reference sample having 100% *streptococcus* (dotted line) and the first derivative of a sample having 100% *Staphylococcus* (solid line);

FIG. 15 represents the first derivative of a reference sample having 100% *streptococcus* (dotted line) and the first derivative of a sample having 50% *streptococcus* and 50% *Staphylococcus* (solid line);

FIG. 16 represents the first derivative of a reference sample having 100% *streptococcus* (dotted line) and the first derivative of a sample having 75% *streptococcus* and 25% *Staphylococcus* (solid line);

FIG. 17 represents the first derivative of a reference sample having 100% *streptococcus* (dotted line) and the first derivative of a sample having 25% *streptococcus* and 75% *Staphylococcus* (solid line).

The m Features Extracted from the Spectrum

The following features were extracted peaks wavelength, peaks height and widths, different peaks' intensity ratios, peaks height ratio. The signal and the signal's first derivative were divided to the above mentioned segments according to said features due to the fact that in that region there were differences between the specific bacteria to be detected (i.e., *streptococcus*) and other bacteria (e.g., *Staphylococcus*).

The $m_1$ Statistical Correlation of Each Segment and the Weighting Factor

The following table, table 4 illustrates the $m_1$ statistical correlation of the signal's first derivative for each segment. The wavenumber ranges are in $cm^{-1}$ and are mentioned in the brackets. Table 4 also presents the weighting factor for each.

TABLE 4 signal's first derivative correlation table

| sample | Correlation1 [1190:990] | Correlation 2 [1363:1235] | Correlation 3 [1650:1550] | Correlation 4 [1780:1720] | Correlation 5 [2995:2836] |
|---|---|---|---|---|---|
| *Strep.* 100% | 0.9966 | 0.988 | 0.9987 | 0.5004 | 0.9987 |
| *Staph.* 100% | 0.7845 | 0.7467 | 0.996 | 0.3735 | 0.9826 |
| *Strep.* 75% | 0.9167 | 0.978 | 0.998 | 0.8102 | 0.9892 |
| *Strep.* 50% | 0.9753 | 0.9016 | 0.9993 | 0.7703 | 0.9888 |
| *Strep.* 25% | 0.9646 | 0.8246 | 0.9979 | 0.4362 | 0.9901 |
| weighting factor | 0.31 | 0.3 | 0.02 | 0.001 | 0.019 |

The following table, table 5 illustrates the $m_1$ statistical correlation of the signal for each segment. The wavenumber ranges are in $cm^{-1}$ and are mentioned in the brackets. Table 5 also presents the weighting factor for each.

TABLE 5 signal correlation table

| sample | Correlation1 [1190:990] | Correlation 2 [1363:1235] | Correlation 3 [1650:1550] | Correlation 4 [1780:1720] | Correlation 5 [2995:2836] |
|---|---|---|---|---|---|
| *Strep.* 100% | 0.99887 | 0.99417 | 0.99985 | 0.99697 | 0.99987 |
| *Staph.* 100% | 0.8719 | 0.97454 | 0.9978 | 0.98574 | 0.99703 |
| *Strep.* 75% | 0.91777 | 0.98977 | 0.99901 | 0.99817 | 0.99775 |
| *Strep.* 50% | 0.99542 | 0.987 | 0.99982 | 0.99563 | 0.99697 |
| *Strep.* 25% | 0.98933 | 0.98857 | 0.99739 | 0.98584 | 0.99598 |
| weighting factor | 0.18 | 0.09 | 0.04 | 0.02 | 0.02 |

The weighting factors of each feature or correlation was determined by the maximum likelihood method.

As can be seen from the tables (4 & 5) correlation 1 and correlation 2 have the largest weighting factor both in the signal and its first derivative. Hence, we will illustrate the calculated boundaries for those correlations.

Boundaries Calculation

As explained above, the boundaries are calculated according to the features and/or statistical correlations which had the most significant contribution for the specific bacteria identification in the sample.

Figure 18:
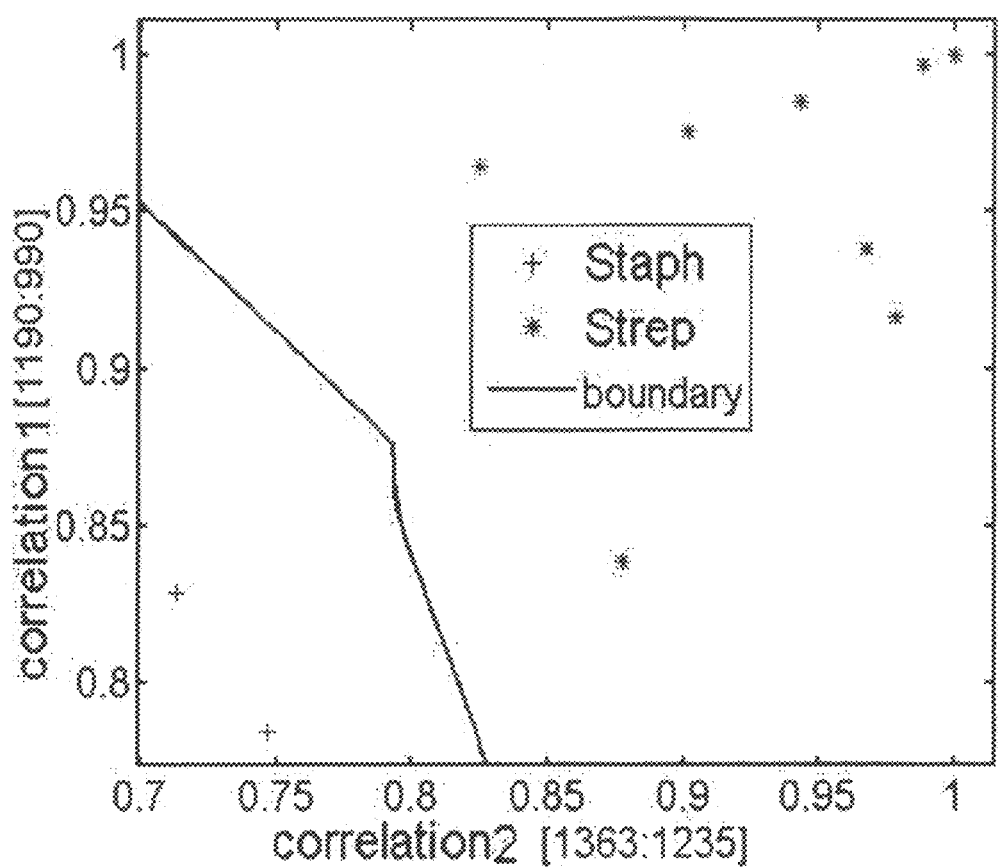
FIG. 18 schematically illustrates the boundaries of a two dimensions area that identifies the bacteria within a dry sample.

Reference is now made to FIG. 18 which illustrate the boundaries of a two dimensions area which enable the identification of bacteria. The boundaries were calculated based on the two features or correlation having the significant contribution to the bacteria prediction—correlation 1 (for the wavenumber ranges of 990 $cm^{-1}$-1190 $cm^{-1}$) and correlation 2 (for the wavenumber ranges of 1235 $cm^{-1}$-1363 $cm^{-1}$) calculated from the first derivative. The specific bacteria to be identified are *streptococcus*.

As can be seen from FIG. 18, when *streptococcus* is present in the sample, it is possible to optically determine and identify its presence within the sample.

Verification Whether the Features or Correlation are within the Boundaries

Once a sample for detection is obtained (for example, a sample containing 50% strep), the absorption signal is read, the first derivative is calculated and data processed. Then, according to the correlations and/or features one can determine whether strep. is present in the sample. The correlations presented in FIG. 18 are the $1^{st}$ and the $2^{nd}$ correlation.

As can be seen from FIG. 15, the $2^{nd}$ correlation (the correlation calculated from the wavenumber range of 1235

$cm^{-1}$-1363 $cm^{-1}$) of the first derivative is 0.9016, the $1^{st}$ correlation (the correlation calculated from the wavenumber range of 990 $cm^{-1}$-1190 $cm^{-1}$) of the first derivative is 0.9753 (FIG. 10).

Referring again to FIG. 18, it can be seen that the point (0.9016, 0.9753) is in the Strep. region—and hence we can inform the patient that strep. is present in the sample.

Let us look at another sample—100% Staph (i.e., no *streptococcus*).

As can be seen from FIG. 14, the $2^{nd}$ correlation (the correlation calculated from the wavenumber range of 1235 $cm^{-1}$-1363 $cm^1$) of the first derivative is 0.7467, the $1^{st}$ correlation (the correlation calculated from the wavenumber range of 990 $cm^{-1}$-1190 $cm^{-1}$) of the first derivative is 0.7845 (FIG. 9).

And from FIG. 18, one can observe that the point (0.7467, 0.7845) is in the Staph. region hence we can inform the patient that strep. is not present in the sample.

Interlinking Between the m Feature and the $m_1$ Correlation to the Specific Bacteria The following feature and correlations were linked to *streptococcus*: peaks 1, 2, 9, 12 13 and 14 from table 3 and the first derivative correlations in the range 990 $cm^{-1}$ to 1190 $cm^{-1}$ and 1235 $cm^{-1}$ to 1363 $cm^{-1}$.

It should be pointed out that the present invention detects bacteria as whole and not just single proteins on the membrane.

Example 4

Distinguishing Between Two Bacteria in a Solution

The following ex-vivo example provides a method to distinguish between two bacteria within a solution. The solution contained a mixture of—*Streptococcus payogenes* and *Staphylococcus aureus*. Furthermore, the ex-vivo example provides a method to identify and to determine whether *Streptococcus* is present within the sample.

The following example provides a method to distinguish between two bacteria in a solution. The solution contained a mixture of—*Streptococcus payogenes* and *Staphylococcus aureus*.

Five mixtures of—*Streptococcus payogenous* and *Staphylococcus aureus* were prepared. The first derivative of the sample's spectroscopic absorption spectrum was then analyzed in different wavelength regions by using Pearson's correlation coefficient as described above.

The mixtures were prepared as follows:

Strep. β hemolytic (lot number 6919) and *Staphylococcus Aureus* (lot number 6985) after third transfer (note: two extra transfers are acceptable before mutations) were purchased from HY Labs, Rehovot, Israel.

Next, two eppendorf tubes were weighted. Then, one stoke solution per brand was prepared. The total volume was of 160 μl+10 swipes with a quadloop from each plat in the two measured plates.

Next, 30 μL of the solutions was put on one marked slot on an optical plate (ZnSe): one slot for the 30 μl Strep and one slot for 30 μl ddH₂O. Then, 30 μL of the solution was put on one marked slot on another optical plate (ZnSe): one slot for the 30 μl Staph and one slot for 30 μl ddH₂O.

Next, the plates were placed in a desiccator (Dessicator 250 mm polypropylene, Yavin Yeda) in the presence of several petri plates with a desiccant agent (Phosphorus Pentoxide cat #79610 Sigma Aldrich) and vacuum was used for 30 minutes.

Next, the two tubes were centrifuged at 14,0000 RPM (HSIANGTAI CNM2000) for 5 minutes. And the supernatant was aspirated. Then, the tubes were weighted and an even concentration was adjusted by diluting the dry bacteria with ddH2O.

The following calculations were recorded:

|  | Weight empty tube | Weight tube + bacteria | Bacteria weight mg | Water added |
|---|---|---|---|---|
| *Streptococcus Pyogenes* | 1.05167 | 1.05814 | 6.47 | 150 μl |
| *Staphylococcus Aureus* | 1.06035 | 1.07268 | 12.33 | 300 μl |

Next, 5 solutions were prepared according to the following table:

| Total volume μl | Strep Pyogenes % (amount to take from master solution in μl) | Staph Aurous CFU/160 μl (amount to take from master solution) |
|---|---|---|
| 60 | 100% (60 μl) | 0% (0 μl) |
| 60 | 75% (45 μl) | 25% (15 μl) |
| 60 | 50% (30 μl) | 50% (30 μl) |
| 60 | 25% (15 μl | 75% (45 μl) |
| 60 | 0 (0 μl) | 0 (0 μl) |
| Total | μL 150 | μL 150 |

Then, the tubes were centrifuged at 140,000 RPM (HSIANGTAI CNM2000) for 5 minutes; and the supernatant was aspirated. Next, 2-3 1 μL droplets were placed on both sides of an optical plate and the spectral signature was read.

The identification and/or detection of specific bacteria was as follows:
- (a) the noise in each of the absorption spectra was reduced by using Savitzky-Golay smoothing;
- (b) the signal's first derivative was calculated;
- (c) m features such as, but not limited to, peaks wavelength, peaks height and widths, peaks height ratio etc. were extracted from the spectra. A total of m features were extracted. m is an integer higher or equals 1;
- (d) the signal and/or its first derivative were divided into several regions (segments) according to said m features;
- (e) $m_1$ statistical correlation were calculated for (i) the spectral signal at each region; and for (ii) the signal derivatives at each region. A total of $m_1$ statistical correlations were extracted. $m_1$ is an integer higher or equals 1. The statistical correlation for the each region (the signal's and its derivatives) was calculated by using Pearson's correlation coefficient;
- (f) the m features and the $m_1$ statistical correlation were examined and checked whether they are within the n dimensional volume boundaries (which acquired by the statistical processing);
- (a) the identification of the specific bacteria was determined as positive if the m features and/or the $m_1$ statistical correlation were within the n dimensional volume boundaries.

Statistical Processing

The statistical processing is especially adapted to provide the n dimensional volume boundaries. For each specific bacterium the statistical processing was performed only once, for obtaining the boundaries. Once the boundaries were provided, the determination whether the specific bacteria is present in a sample was as explained above (i.e., verifying whether the features or correlation are within the boundaries).

Furthermore, once the boundaries were provided, there exists no need for the statistical processing of the same specific bacteria again.

The statistical processing for each specific bacterium is performed in the following manner:
- (a) obtaining several absorption spectrum (AS2) of samples containing the specific bacteria;
- (b) extracting x features, from said AS2, such as, but not limited to, peaks wavelength, peaks height and widths, different peaks' intensity ratios etc. were extracted from the spectra. A total of x features. x is an integer higher or equals 1;
- (c) calculating the signal's first derivative;
- (d) dividing the signal and/or its first derivative into several regions (segments) according to said x features;
- (e) Calculating the y correlation for the different segments within the absorption spectrums;
- (f) Defining n dimensional space. n equals the sum of the x features and the y statistical correlations;
- (g) Assigning and/or interlinking each one of the x feature, and each one of the y correlation to the specific bacteria which its identification is required;
- (h) Calculating the Gaussian distribution for (i) each of the x feature; and/or for (ii) each of the y statistical correlations. All the calculated Gaussian distributions constitute an n dimensional volume in the n dimensional space; and,
- (i) Determining the boundaries of each volume by using quadratic Gaussian classifier or similar method (for example k nearest neighbor, Bayesian classification et cetera).

If the features and correlation (extracted from the spectrum) are within the n dimensional volume boundaries, the specific bacteria are identified. Otherwise the bacteria are not identified.

Alternatively or additionally, each of the x feature and/or for the y statistical correlations is given a weighting factor. The weighting factor is determined by the examining how each feature or correlation improves the bacteria detection prediction (for example by using maximum likelihood or Bayesian estimation). Once the weighting factor is assigned to each one of the x feature and the y statistical correlations, the boundaries are determined for the features and/or the statistical correlations having the most significant contribution to the bacteria prediction. Alternatively or additionally, the AS2 is smoothed by reducing the noise. The noise reduction is obtained by different smoothing techniques selected from a group consisting of running average savitzky-golay or any combination thereof.

We'll first present an example for the smoothing technique. For that the entire signal and its first derivative prior to and after the noise are presented.

Then will give examples for the deviation of the spectrum. And lastly an example of the boundaries is given. It should be pointed put that for demonstrating purposes the boundaries were calculated according to the features and/or statistical correlations which had the most significant contribution are given for the samples.

Furthermore, the object of the following examples is to identify *streptococcus*.

Smoothing of the Spectrum

Figure 19:
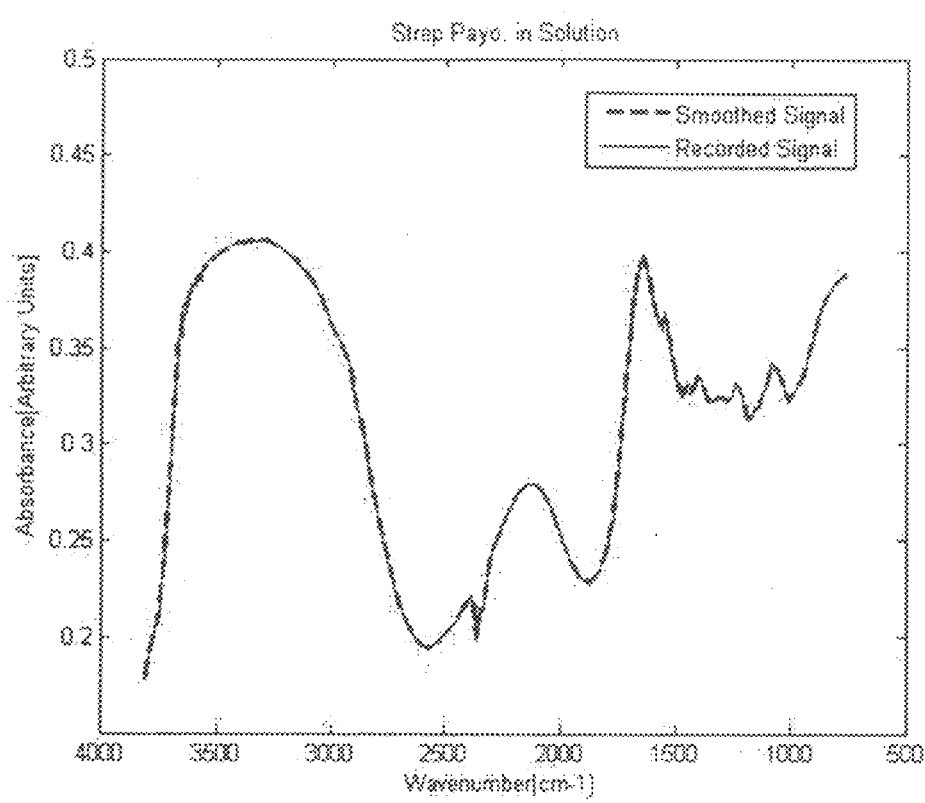
FIG. 19 illustrates the absorption signal of a sample containing 100% *streptococcus* prior to and after the noise was reduced.

Reference is now made to FIG. 19 illustrating the absorption signal of a sample containing 100% *streptococcus* prior to and after the noise was reduced (recorded signal vs. smoothed signal).

Figure 20:
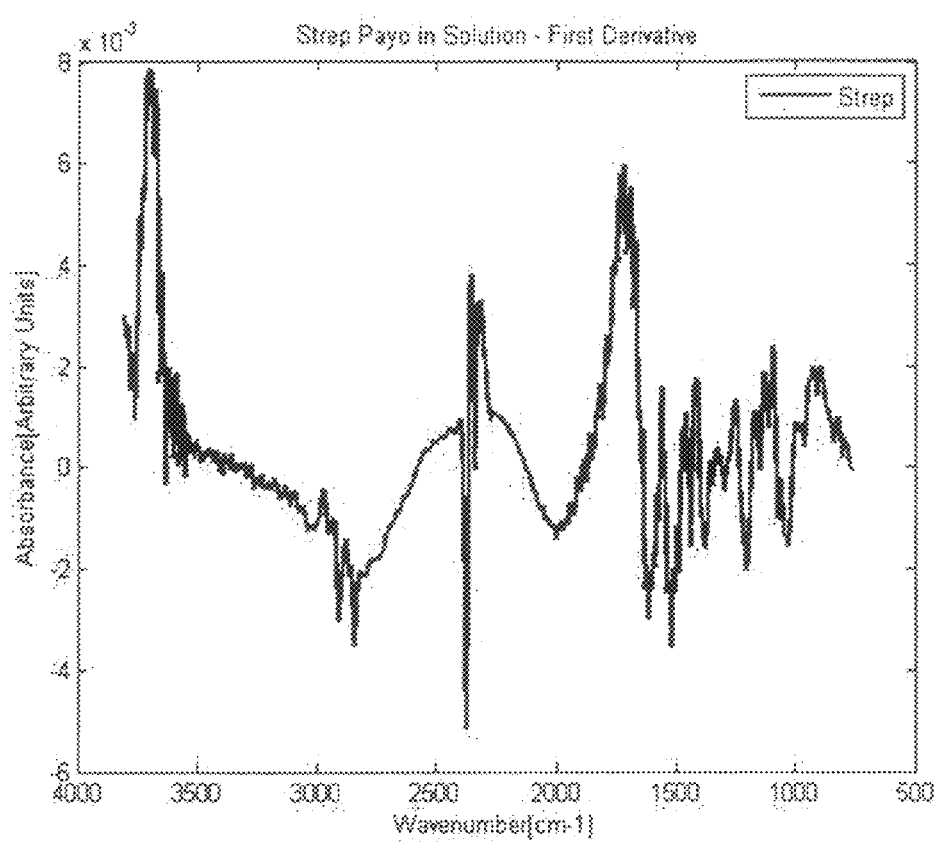
FIG. 20 illustrates the first derivative of the absorption signal in a sample containing 100% *streptococcus* prior to and after the noise was reduced.

Reference is now made to FIG. 20 illustrating the signal's first derivative of a sample containing 100% *streptococcus* prior to and after the noise was reduced (recorded signal vs. smoothed signal).

Dividing the Absorption Spectrum and its First Derivative

The first derivative of an absorption spectrum of different samples (having different amount of *streptococcus* and *Staphylococcus*) are given. The first derivatives are given as example in three selected segments ($950$ $cm^{-1}$ to $1200$ $cm^{-1}$; $1220$ $cm^{-1}$ to $1380$ $cm^{-1}$; and $1710$ $cm^{-1}$ to $1780$ $cm^{-1}$).

The entire segments (as divided both for the signal and the first derivative) are listed in table 5 and 6 along with the correlations.

Figure 21:
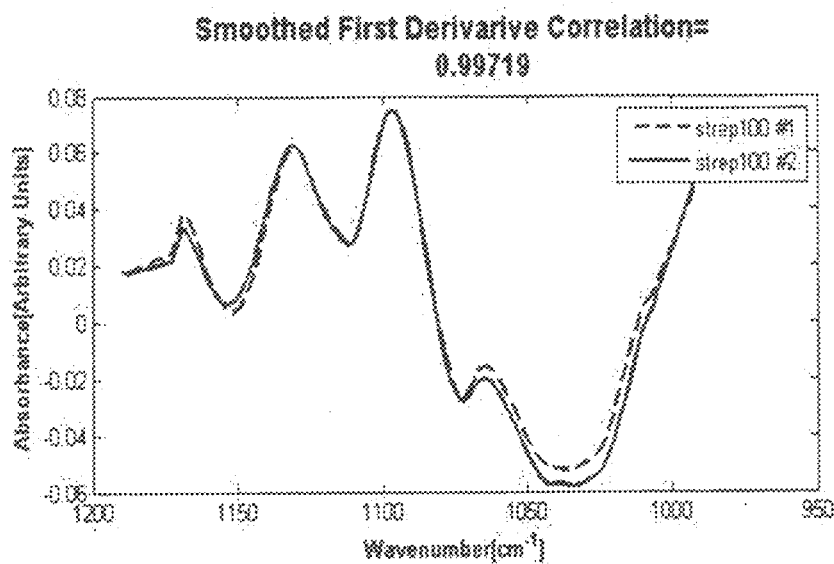
FIGS. 21-23 illustrate the first derivative of the absorption spectrum of a reference sample containing 100% *Streptococ-* cus, a sample containing 100% *Streptococcus* and the corresponding statistical correlations.
Figure 22:
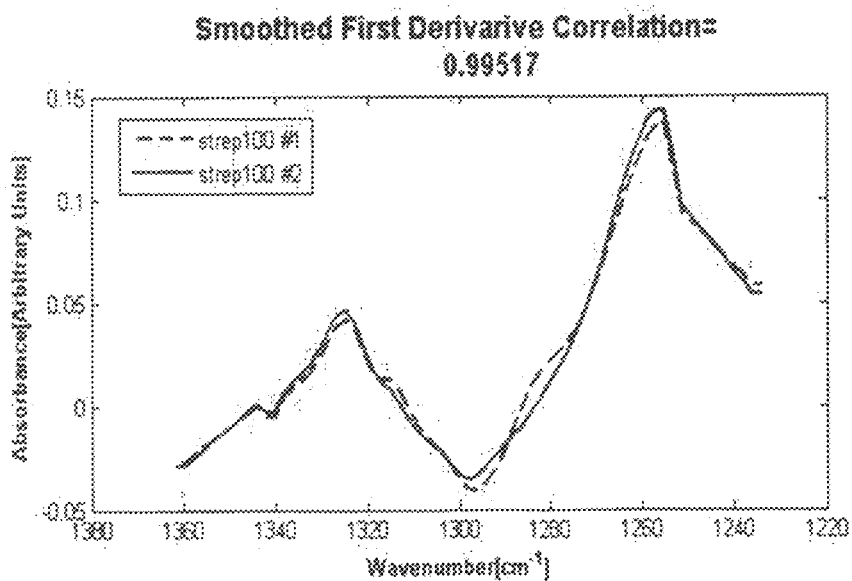
Figure 23:
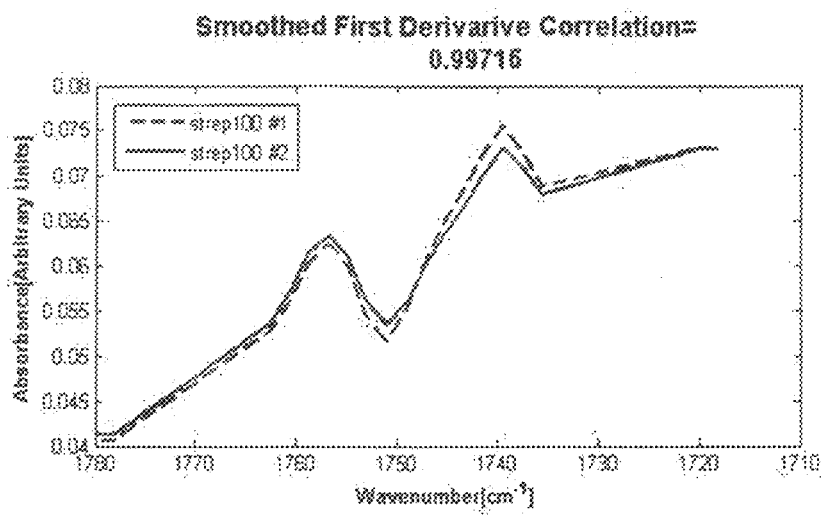

Reference is now made to FIGS. 21-23 which illustrate the first derivative of the absorption spectrum of a reference sample containing 100% *Streptococcus* (dotted line), a sample containing 100% *Streptococcus*(solid line), and the corresponding statistical correlations.

FIG. 21 illustrates the reference sample's and sample's first derivative in the first range region of $950$ $cm^{-1}$ to $1200$ $cm^{-1}$. FIG. 22 illustrates the reference sample's and the sample's first derivative in the second region of $1220$ $cm^{-1}$ to $1380$ $cm^{-1}$. FIG. 23 illustrates the reference sample's and the sample's first derivative in the third region of $1710$ $cm^{-1}$ to $1780$ $cm^{-1}$.

Reference is now made to FIGS. 24-26 which illustrate the first derivative of the absorption spectrum of a reference sample containing 100% *Streptococcus* (dotted line) and a sample containing 100% *Staphylococcus* (solid line). The figures also present the corresponding statistical correlations.

FIG. 24 illustrates the reference sample's and the sample's first derivative in the first range region of $950$ $cm^{-1}$ to $1200$ $cm^{-1}$.

FIG. 25 illustrates the reference sample's and the sample's first derivative in the second region of $1220$ $cm^{-1}$ to $1380$ $cm^{-1}$.

FIG. 26 illustrates the reference sample's and the sample's first derivative in the third region of $1710$ $cm^{-1}$ to $1780$ $cm^{-1}$.

Reference is now made to FIGS. 27-29 which illustrate the first derivative of the absorption spectrum of a reference sample containing 100% *Streptococcus* (dotted line) and a sample containing 50% *Staphylococcus* and 50% *Streptococcus* (solid line). The figures also present the corresponding statistical correlations.

FIG. 27 illustrates the reference sample's and the sample's first derivative in the first range region of $950$ $cm^{-1}$ to $1200$ $cm^{-1}$.

FIG. 28 illustrates the reference sample's and the sample's first derivative in the second region of $1220$ $cm^{-1}$ to $1380$ $cm^{-1}$.

FIG. 29 illustrates the reference sample's and the sample's first derivative in the third region of $1710$ $cm^{-1}$ to $1780$ $cm^{-1}$.

Reference is now made to FIGS. 30-32 which illustrate the first derivative of the absorption spectrum of a reference sample containing 100% *Streptococcus* (dotted line) and a sample containing 25% *Staphylococcus* and 75% *Streptococcus* (solid line). The figures also present the corresponding statistical correlations.

FIG. 30 illustrates the reference sample's and the sample's first derivative in the first range region of $950$ $cm^{-1}$ to $1200$ $cm^{-1}$.

FIG. 31 illustrates the reference sample's and the sample's first derivative in the second region of $1220$ $cm^{-1}$ to $1380$ $cm^{-1}$.

FIG. 32 illustrates the reference sample's and the sample's first derivative in the third region of $1710$ $cm^{-1}$ to $1780$ $cm^{-1}$.

Reference is now made to FIGS. 33-35 which illustrate the first derivative of the absorption spectrum of a reference sample containing 100% *Streptococcus* (dotted line) and a sample containing 75% *Staphylococcus* and 25% *Streptococcus* (solid line). The figures also present the corresponding statistical correlations.

FIG. 33 illustrates the reference sample's and the sample's first derivative in the first range region of 950 $cm^{-1}$ to 1200 $cm^{-1}$.

FIG. 34 illustrates the reference sample's and the sample's first derivative in the second region of 1220 $cm^{-1}$ to 1380 $cm^{-1}$.

FIG. 35 illustrates the reference sample's and the sample's first derivative in the third region of 1710 $cm^{-1}$ to 1780 $cm^{-1}$.

The m Features Extracted from the Spectrum

The following features were extracted peaks wavelength, peaks height and widths, different peaks' intensity ratios, peaks height ratio. The signal and the signal's first derivative were divided to the above mentioned segments according to said features due to the fact that in that region there were differences between the specific bacteria to be detected (i.e., *streptococcus*) and other bacteria (e.g., *Staphylococcus*).

The $m_1$ Statistical Correlation of Each Segment and the Weighting Factor

The following table, table 6 illustrates the $m_1$ statistical correlation of the signal's first derivative for each segment. The wavenumber ranges are in $cm^{-1}$ and are mentioned in the brackets. Table 6 also presents the weighting factor for each.

The weighting factors of each feature or correlation was determined by the maximum likelihood method.

As can be seen from the tables (6 & 7) correlation 1 and correlation 4 have the largest weighting factor both in the signal and its first derivative. Hence, we will illustrate the calculated boundaries for those correlations.

Boundaries Calculation

As explained above, the boundaries are calculated according to the features and/or statistical correlations which had the most significant contribution for the specific bacteria identification in the samples.

Reference is now made to FIG. 36 which illustrate the boundaries of a two dimensions area which enable the identification of bacteria. The boundaries were calculated based on the two features or correlation having the significant contribution to the bacteria prediction—correlation 1 (for the wavenumber ranges of 990 $cm^{-1}$-1190 $cm^{-1}$) and correlation 2 (for the wavenumber ranges of 1235 $cm^{-1}$-1363 $cm^{-1}$) calculated from the first derivative. The specific bacteria to be identified are *streptococcus*.

As mentioned, the boundaries of the correlation values as well as for the other features are determined by the quadratic Gaussian classifier or similar method.

Again, as can be seen from FIG. 36 and as was demonstrated in the dry samples, when *streptococcus* is present in the sample, it is possible to optically determine and identify its presence within the sample.

TABLE 6 signal's first derivative correlation table

| sample | Correlation1 [1190:990] | Correlation 2 [1363:1235] | Correlation 3 [1650:1550] | Correlation 4 [1780:1720] | Correlation 5 [2995:2836] |
|---|---|---|---|---|---|
| Strep. 100% | 0.99719 | 0.99517 | 0.98354 | 0.99716 | 0.99794 |
| Staph. 100% | 0.89313 | 0.91064 | 0.89163 | −0.43181 | 0.98581 |
| Strep. 75% | 0.98223 | 0.98223 | 0.98703 | 0.86995 | 0.99619 |
| Strep. 50% | 0.91633 | 0.95679 | 0.83732 | −0.1747 | 0.98709 |
| Strep. 25% | 0.90358 | 0.93308 | 0.83065 | −0.19636 | 0.99509 |
| weighting factor | 0.27 | 0.18 | 0.01 | 0.3 | 0.05 |

The following table, table 7 illustrates the $m_1$ statistical correlation of the signal for each segment. The wavenumber ranges are in $cm^{-1}$ and are mentioned in the brackets. Table 7 also presents the weighting factor for each.

Verification Whether the Features or Correlation are within the Boundaries

Once a sample for detection is obtained (for example, a sample containing 25% strep), the absorption signal is read,

| sample | Correlation1 [1190:990] | Correlation 2 [1363:1235] | Correlation 3 [1650:1550] | Correlation 4 [1780:1720] | Correlation 5 [2995:2836] |
|---|---|---|---|---|---|
| Strep. 100% | 0.99097 | 0.99954 | 0.99237 | 0.99997 | 0.99923 |
| Staph. 100% | 0.97118 | 0.99099 | 0.90992 | 0.99441 | 0.99516 |
| Strep. 75% | 0.98197 | 0.9858 | 0.93361 | 0.99329 | 0.99692 |
| Strep. 50% | 0.98696 | 0.99762 | 0.99266 | 0.99921 | 0.99983 |
| Strep. 25% | 0.96841 | 0.98883 | 0.85486 | 0.99385 | 0.98444 |
| weighting factor | 0.09 | 0.005 | 0.005 | 0.01 | 0.09 | the first derivative is calculated and data processed. Then according to the correlations and/or features one can determine whether strep. is present in the sample. The correlations presented in FIG. 36 are the $1^{st}$ and the $4^{th}$ correlation.

As can be seen from FIG. 35, the $4^{th}$ correlation (the correlation calculated from the wavenumber range of 1720 cm$^{-1}$-1780 cm$^{-1}$) of the first derivative is −0.1936, the $1^{st}$ correlation (the correlation calculated from the wavenumber range of 990 cm$^{-1}$-1190 cm$^{-1}$) of the first derivative is 0.90358 (FIG. 33).

Referring again to FIG. 36, it can be seen that the point (−0.1936, 0.90358) is in the Strep. region—and hence we can inform the patient that strep. is present in the sample.

Let us look at another sample-100% Staph (i.e., no *streptococcus*).

As can be seen from FIG. 26, the $4^{th}$ correlation (the correlation calculated from the wavenumber range of 1720 cm$^{-1}$-1780 cm$^{-1}$) of the first derivative is −0.43181, the $1^{st}$ correlation (the correlation calculated from the wavenumber range of 990 cm$^{-1}$-1190 cm$^{-1}$) of the first derivative is 0.89313 (FIG. 24).

And from FIG. 36, one can observe that the point (−0.43181, 0.89313) is in the Staph. region—hence we can inform the patient that strep. is not present in the sample.

Interlinking Between the M Feature and the $m_1$ Correlation to the Specific Bacteria The following feature and correlations were linked to *streptococcus* peaks 1, 2, 9, 12 13 and 14 from table 3 and the first derivative correlations in the range 990 cm$^{-1}$ to 1190 cm$^{-1}$ and 1235 cm$^{-1}$ to 1363 cm$^{-1}$.

It should be pointed out that the present invention detects bacteria as whole and not just single proteins on the membrane.

Furthermore, it should be pointed out that in this specific example the water influence was not eliminated. And hence, it is within the scope of the present invention to identify bacteria without eliminating the water influence.

The invention claimed is:

1. A method for determining whether a particular type of bacteria is found within an uncultured sample, wherein said method comprises:
    placing said uncultured sample in a sample compartment of an infrared spectrometer;
    obtaining, by use of said infrared spectrometer, an infrared absorption spectrum (AS) of said uncultured sample, said AS containing water influence;
    determining volume boundaries for an n-dimensional space for said particular type of bacteria by:
        placing a sample containing said particular type of bacteria in the sample compartment of an infrared spectrometer;
        obtaining, by used of said infrared spectrometer, a second infrared absorption spectrum (AS2) of said sample containing said particular type of bacteria;
        extracting x features from said AS2 selected from the group consisting of peak wavelength, peak height, peak width, different peaks' intensity ratios and any combination thereof;
        calculating at least one derivative of said AS2;
        dividing said AS2 into y segments according to said x features;
        calculating a statistical correlation for each of said segments;
        calculating a weighting factor for each of said statistical correlations;
        choosing n≤x+y most highly weighted statistical correlations as dimensions of said n-dimensional space;
        assigning each one of said features and each one of said correlations to said particular type of bacteria; and,
        determining said boundaries of said n dimensional volume by using a technique selected from the group consisting of quadratic Gaussian classifier, k nearest neighbor, Bayesian classification and any combination thereof; and,
    eliminating said water influence from said AS to produce an AS without said water influence by:
        providing the absorption intensity $\text{Sig}_{with\ water}(\tilde{v})$ at each wavenumber $\tilde{v}$ within said AS;
        dividing said AS into at least two wavenumber ranges;
        calculating the correction factors $CF(\tilde{v})$ at each wavenumber $\tilde{v}$ within said at least two ranges;
        acquiring from said AS at least one feature that is influenced by said water, said feature extending over a wavenumber range $\tilde{v}_1$-$\tilde{v}_n$;
        calculating $\text{Sig}_{water\ only}(\tilde{v}_q)$ at each of q predetermined wavenumbers $\tilde{v}_q$ within said wavenumber range $\tilde{v}_1$-$\tilde{v}_n$, q>1;
        calculating a correction factor $CF_{water\ only}(\tilde{v}_q)$ at each of said q predetermined wavenumbers;
        dividing said $\text{Sig}_{water\ only}(\tilde{v}_q)$ by said $CF_{water\ only}(\tilde{v}_q)$ at each of said q wavenumbers, thereby obtaining q ratios $\text{Sig}_{water\ only}(\tilde{v}_q)/CF_{water\ only}(\tilde{v}_q)$;
        calculating the average of said q ratios AVG$[\text{Sig}_{water\ only}(\tilde{v}_q)/CF_{water\ only}(\tilde{v}_q)]$;
        multiplying said AVG$[\text{Sig}_{water\ only}(\tilde{v}_q)/CF_{water\ only}(\tilde{v}_q)]$ by said $CF(\tilde{v})$ at each wavenumber $\tilde{v}$ within said AS; and,
        subtracting the product of the multiplication performed in the previous step from said $\text{Sig}_{with\ water}(\tilde{v})$ at each at each wavenumber $\tilde{v}$ within said AS;
    processing said AS without said water influence by:
        smoothing said AS without said water influence by using a technique selected from the group consisting of running average, Savitzky-Golay, and any combination thereof;
        extracting m features from said AS selected from a group consisting of peak width, peak intensity, the ratio width/intensity, peak wavelength, different peaks' intensity ratios, and any combination thereof wherein m≥1;
        dividing said AS into $m_1$ segments according to said m features; and,
        calculating a statistical correlation for each of said segments;
    wherein said particular type of bacteria is determined to be present in said uncultured sample if said statistical correlation $m_1$ and/or said m features are within said n dimensional volume determined from said second infrared spectrum AS2.

2. The method according to claim 1, wherein said step of data processing said AS without said water influence additionally comprises:
    calculating at least one of the $o^{th}$ derivatives of said AS, wherein o is an integer ≥1;
    extracting $m_2$ features from said $o^{th}$ derivative selected from the group consisting of peak width, peak intensity, the ratio width/intensity, different peaks' intensity ratios, peak wavelength, and any combination thereof;
    dividing said $o^{th}$ derivative into several segments according to said $m_2$ features; and,
    calculating the $m_3$ statistical correlation in each of said segments;
wherein said particular type of bacteria is determined to be present in said uncultured sample if said $m_1$ and/or $m_3$ statistical correlation and/or said m and/or said $m_2$ features are within said n dimensional volume determined from said second infrared spectrum AS2.

3. The method according to claim 2, wherein said step of calculating a statistical correlation in each of said segments is performed by calculating Pearson's correlation coefficient.

4. The method according to claim 1, additionally comprising selecting said particular type of bacteria from the group consisting of *Streptococcus Pyogenes*, Group C and G beta-hemolytic Streptococci, *Corynebacterium haemolyticum*, Diphtheria, Ulcerans, *Neisseria gonorrhoeae, Mycoplasma pneumoniae, Yersinia enterocolitica, Mycobacterium tuberculosis, Chlamydia trachomatiss, Pneumoniae, Bordetella Pertussis, Legionella* spp, *Pneumocystis Carinii, Norcardia, Histoplasma Capsulatum, Coccidioides Immitis, Haemophilus influenza* group A beta hemolytic and *staphylococcus Aureus*.

5. The method according to claim 1, additionally comprising analyzing said AS in at least one region selected from the group consisting of about 3000-3300 cm$^{-1}$; about 850-1150 cm$^{-1}$; and about 1300-1350 cm$^{-1}$.

6. The method according to claim 1, wherein said step of calculating weighting factors is performed by a method selected from the group consisting of maximum likelihood and Bayesian estimation.

7. The method according to claim 1, wherein said step of calculating weighting factors is performed according to the following algorithm:

for $\tilde{v}$ between 1846 cm$^{-1}$ and 2613 cm$^{1}$:

$$CF(\tilde{v})=a_{11}e^{(-((\tilde{v}-b11)/c11)^2)}+a_{21}e^{(-((\tilde{v}-b21)/c21)^2)}+a_{31}e^{(-((\tilde{v}-b31)/c31)^2)}+a_{41}e^{(-((\tilde{v}-b41)/c41)^2)}+a_{51}e^{(-((\tilde{v}-b51)/c51)^2)}+a_{61}e^{(-((\tilde{v}-b61)/c61)^2)}+a_{71}e^{(-((\tilde{v}-b71)/c71)^2)}+a_{81}e^{(-((\tilde{v}-b81)/c81)^2)}$$

wherein $a_{11}$=137.2; $b_{11}$=2170; $c_{11}$=224.3; $a_{21}$=19.02; $b_{21}$=2063; $c_{21}$=37.53; $a_{31}$=0.7427; $b_{31}$=2224; $c_{31}$=13; $a_{41}$=98.33; $b_{41}$=2124; $c_{41}$=109.8; $a_{51}$=-4.988; $b_{51}$=2192; $c_{51}$=33.87; $a_{61}$=20.19; $b_{61}$=1998; $c_{61}$=40.22; $a_{71}$=228.3; $b_{71}$=1496; $c_{71}$=1329; $a_{81}$=6.751×10$^{12}$; $b_{81}$=-1226; and, $c_{81}$=592.1;

for $\tilde{v}$ between 1461 cm$^{-1}$ and 1846 cm$^{-1}$:

$$CF(\tilde{v})=a_{12}e^{(-((\tilde{v}-b12)/c21)^2)}+a_{22}e^{(-((\tilde{v}-b22)/c22)^2)}+a_{32}e^{(-((\tilde{v}-b32)/c32)^2)}+a_{42}e^{(-((\tilde{v}-b42)/c42)^2)}+a_{52}e^{(-((\tilde{v}-b52)/c52)^2)}+a_{62}e^{(-((\tilde{v}-b62)/c62)^2)}+a_{72}e^{(-((\tilde{v}-b72)/c72)^2)}+a_{82}e^{(-((\tilde{v}-b82)/c82)^2)}$$

wherein $a_{12}$=-300.2; $b_{12}$=1650; $c_{12}$=13.65; $a_{22}$=-51.65; $b_{22}$=1665; $c_{22}$=6.48; $a_{32}$=142.4; $b_{32}$=1623; $c_{32}$=7.584; $a_{42}$=1450; $b_{42}$=1649; $c_{42}$=32.62; $a_{52}$=96.34; $b_{52}$=1617; $c_{52}$=2.387; $a_{62}$=608; $b_{62}$=1470; $c_{62}$=369.3; $a_{72}$=0; $b_{72}$=1873; $c_{72}$=2.625; $a_{82}$=1037; $b_{82}$=1644; and, $c_{82}$=76.21;

for $\tilde{v}$ between 1111 cm$^{-1}$ and 1461 cm$^{-1}$:

$$CF(\tilde{v})=a_{13}e^{(-((\tilde{v}-b13)/c13)^2)}+a_{23}e^{(-((\tilde{v}-b23)/c23)^2)}+a_{33}e^{(-((\tilde{v}-b33)/c33)^2)}+a_{43}e^{(-((\tilde{v}-b43)/c43)^2)}+a_{53}e^{(-((\tilde{v}-b53)/c53)^2)}+a_{63}e^{(-((\tilde{v}-b63)/c63)^2)}+a_{73}e^{(-((\tilde{v}-b73)/c73)^2)}+a_{83}e^{(-((\tilde{v}-b83)/c83)^2)}$$

wherein $a_{13}$=1368; $b_{13}$=2167; $c_{13}$=767; $a_{23}$=80.67; $b_{23}$=1356; $c_{23}$=68.83; $a_{33}$=36.85; $b_{33}$=1307; $c_{33}$=33.79; $a_{43}$=142.5; $b_{43}$=1244; $c_{43}$=67.19; $a_{53}$=260.4; $b_{53}$=1130; $c_{53}$=88.91; $a_{63}$=66.54; $b_{63}$=1093; $c_{63}$=31; $a_{73}$=7.126; $b_{73}$=1345; $c_{73}$=20.9; $a_{83}$=4.897; $b_{83}$=1280; and, $c_{83}$=11.05;

for $\tilde{v}$ between 961 cm$^{-1}$ and 1111 cm$^{-1}$:

$$CF(\tilde{v})=a_{14}e^{(-((\tilde{v}-b14)/c14)^2)}+a_{24}e^{(-((\tilde{v}-b24)/c24)^2)}+a_{34}e^{(-((\tilde{v}-b34)/c34)^2)}+a_{44}e^{(-((\tilde{v}-b44)/c44)^2)}+a_{54}e^{(-((\tilde{v}-b54)/c54)^2)}+a_{64}e^{(-((\tilde{v}-b64)/c64)^2)}+a_{74}e^{(-((\tilde{v}-b74)/c74)^2)}+a_{84}e^{(-((\tilde{v}-b84)/c84)^2)}$$

wherein $a_{14}$=692.6; $b_{14}$=952; $c_{14}$=31.04; $a_{24}$=48.46; $b_{24}$=983.2; $c_{24}$=15.72; $a_{34}$=287.5; $b_{34}$=994.6; $c_{34}$=27.98; $a_{44}$=434.9; $b_{44}$=1032; $c_{44}$=40.86; $a_{54}$=17.05; $b_{54}$=1052; $c_{54}$=13.55; $a_{64}$=48.61; $b_{64}$=1068; $c_{64}$=16.56; $a_{74}$=70.71; $b_{74}$=1086; $c_{74}$=21.23; $a_{84}$=497.3; $b_{84}$=1124; and, $c_{84}$=64.42;

and,
for $\tilde{v}$ between 570 cm$^{-1}$ and 961 cm$^{-1}$:

$$CF(\tilde{v})=a_{15}e^{(-((\tilde{v}-b15)/c15)^2)}+a_{25}e^{(-((\tilde{v}-b25)/c25)^2)}+a_{35}e^{(-((\tilde{v}-b35)/c35)^2)}+a_{45}e^{(-((\tilde{v}-b45)/c45)^2)}+a_{55}e^{(-((\tilde{v}-b55)/c55)^2)}+a_{65}e^{(-((\tilde{v}-b65)/c65)^2)}+a_{75}e^{(-((\tilde{v}-b75)/c75)^2)}+a_{85}e^{(-((\tilde{v}-b85)/c85)^2)}$$

wherein $a_{15}$=-2877; $b_{15}$=36.23; $c_{15}$=29.09; $a_{25}$=0; $b_{25}$=-124.3; $c_{25}$=22.09; $a_{35}$=-190.7; $b_{35}$=18.97; $c_{35}$=16.45; $a_{45}$=1.589×10$^4$; $b_{45}$=-3.427; $c_{45}$=56.25; $a_{55}$=-1.352×10$^4$; $b_{55}$=-5.861; $c_{55}$=40.75; $a_{65}$=476.7; $b_{65}$=82.38; $c_{65}$=17.29; $a_{75}$=1286; $b_{75}$=62.29; $c_{75}$=180.3; $a_{85}$=802.9; $b_{85}$=102.8; and, $c_{85}$=18.79.

* * * * *